US008961607B2

(12) United States Patent
Bucci

(10) Patent No.: US 8,961,607 B2
(45) Date of Patent: Feb. 24, 2015

(54) COMBINED SPINAL INTERBODY AND PLATE ASSEMBLIES

(75) Inventor: Kara A. Bucci, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 13/614,823

(22) Filed: Sep. 13, 2012

(65) Prior Publication Data
US 2013/0006367 A1 Jan. 3, 2013

Related U.S. Application Data

(63) Continuation of application No. 12/836,285, filed on Jul. 14, 2010, now Pat. No. 8,343,223.

(60) Provisional application No. 61/225,356, filed on Jul. 14, 2009.

(51) Int. Cl.
*A61F 2/44* (2006.01)
*A61B 17/86* (2006.01)
*A61F 2/30* (2006.01)

(52) U.S. Cl.
CPC .............. *A61F 2/4455* (2013.01); *A61B 17/86* (2013.01); *A61F 2002/30369* (2013.01); *A61F 2002/30471* (2013.01); *A61F 2002/30578* (2013.01); *A61F 2002/30787* (2013.01); *A61F 2002/30794* (2013.01); *A61F 2002/30904* (2013.01); *A61F 2002/4475* (2013.01); *A61F 2220/0033* (2013.01)
USPC ..................................... 623/17.16; 623/17.11

(58) Field of Classification Search
USPC ........................................... 623/17.11–17.16
See application file for complete search history.

(56) References Cited

U.S. PATENT DOCUMENTS

| 6,176,882 | B1 | 1/2001 | Biedermann et al. |
| 2005/0085913 | A1* | 4/2005 | Fraser et al. ............... 623/17.11 |
| 2005/0102028 | A1 | 5/2005 | Arnin et al. |

(Continued)

FOREIGN PATENT DOCUMENTS

WO WO-2008-065443 6/2008

OTHER PUBLICATIONS

Written Opinion of the International Searching Authority for International Application No. PCT/US2010/041983, mail date Sep. 10, 2010, 5 pages.

(Continued)

*Primary Examiner* — Jerry Cumberledge
*Assistant Examiner* — Nicholas Plionis
(74) *Attorney, Agent, or Firm* — Foley & Lardner LLP

(57) ABSTRACT

A spinal implant assembly combines a spinal interbody spacer with a spine plate. The combined spacer and plate assembly provides stabilization and torsional resistance to promote fusion of adjacent vertebrae. The spacer is configured for placement within an intervertebral space between the adjacent vertebrae previously occupied by a spinal disc. The plate is configured for attachment to anterior sides of the adjacent vertebrae. Translation of the spinal plate allows it to be affixed to the vertebrae in various positions and/or allow movement post installation. In one form, the plate is defined by first and second spine plate or plate portions that are coupled to one another to allow rotation about each other. Ends of the first and second spine plates are received in/by the interbody spacer, while a pin extends through the interbody spacer to fix the first and second spine plates to the interbody spacer.

13 Claims, 21 Drawing Sheets

(56) References Cited

U.S. PATENT DOCUMENTS

| | | |
|---|---|---|
| 2005/0216081 A1 | 9/2005 | Taylor |
| 2006/0100708 A1 | 5/2006 | Link et al. |
| 2007/0219635 A1* | 9/2007 | Mathieu et al. ............ 623/17.16 |
| 2008/0183294 A1 | 7/2008 | Adl |
| 2008/0249625 A1 | 10/2008 | Waugh et al. |
| 2009/0076608 A1 | 3/2009 | Gordon et al. |
| 2009/0182430 A1* | 7/2009 | Tyber et al. ................ 623/17.16 |
| 2010/0070037 A1 | 3/2010 | Parry et al. |
| 2010/0249937 A1 | 9/2010 | Blain et al. |

OTHER PUBLICATIONS

International Search Report for International Application No. PCT/US2010/041983, mail date Sep. 10, 2010, 1 page.

* cited by examiner

COMBINED SPINAL INTERBODY AND PLATE ASSEMBLIES

CROSS-REFERENCE TO RELATED APPLICATIONS

The present application is a continuation of U.S. patent application Ser. No. 12/836,285 filed Jul. 14, 2010 which claims priority to U.S. Provisional Patent Application Ser. No. 61/225,356 filed Jul. 14, 2009, entitled "Combined Spinal Interbody and Plate Assemblies", both of which are hereby incorporated herein by reference.

BACKGROUND

The present invention relates to spinal implants for the stabilization, distraction, support and/or the promotion of bone fusion between adjacent vertebrae of the spine.

Background Information

Because of disease, injury or deformity the disc that is between adjacent vertebrae of the human spine may become damaged. Additionally, the disc may simply deteriorate due to age or congenital defect. In these and in other circumstances, one or more vertebrae may become compressed or otherwise damaged. Moreover, the vertebrae can become too closely spaced which causes an undesired abnormal curvature of the spine. Such conditions may also cause a nerve to be pinched, creating pain, numbness and/or other symptoms. In these situations it is then necessary to provide support and/or alignment to and between adjacent vertebrae of the patient's spine. This is generally accomplished through spinal surgery.

With spinal surgery, one or more spinal implants, spacers, intervertebral devices or interbody devices (collectively, spinal spacers) are placed between adjacent vertebrae once the disc has been removed. This provides proper spacing of the vertebrae. The spinal spacer may also promote fusion between the adjacent vertebrae.

Once the spinal spacer has been implanted into the intervertebral space, it is important that the spinal spacer remain in its implanted position. In addition to remaining in place, the spinal spacer must also be able to handle the load that is imparted thereto from the adjacent vertebrae.

Accordingly, there exists a need for a spinal spacer that remains in place once implanted and provides stabilization and torsional resistance to promote fusion.

SUMMARY

The present invention is a spinal prosthesis or implant comprising a combined spinal interbody spacer and plate assembly. The combined spinal interbody spacer and plate assembly provides stabilization and torsional resistance to promote fusion of adjacent vertebrae of the spine.

The interbody spacer of the combined spinal interbody spacer and plate assembly is configured for placement within an intervertebral space between adjacent vertebrae previously occupied by a spinal disc. The spinal plate thereof is configured for attachment to anterior sides of the adjacent vertebrae (either on or within the vertebrae).

The spinal plate may dynamize, adjust or translate relative to the interbody spacer, or it may be static or fixed relative to the interbody spacer. Movement of the spinal plate allows it to be affixed to the vertebrae in various positions and/or allow movement post installation. The spinal plate may be positioned to provide initial compression of the vertebrae, allow or not allow post installation compression or provide other post installation movement. Accordingly, the spinal plate may further translate during further vertebral movement (e.g. compression) depending on the initial fixation position thereof.

In one form, the spinal plate is defined by first and second spine plates or plate portions that are coupled to one another to allow rotation about each other. Rotation provides for variable spine plate positioning and/or relative motion of the plates post installation. In one form, the first and second spine plates are coupled via a pin to allow rotation about each other. Ends of the first and second spine plates are received in/by the interbody spacer, while the pin extends through the interbody spacer to fix the first and second spine plates to the interbody spacer.

The pin may be retained by the interbody spacer so as to allow an anterior/posterior sliding motion between the pin and the interbody spacer such that the position of the interbody spacer within the intervertebral space does not change when the first and second spine plates rotate during compression of the adjacent vertebrae.

The spine plates may be mounted relative to or on the adjacent vertebrae to either allow rotation of the plates or not allow rotation of the plates during compression of the adjacent vertebrae. If the spine plates are mounted to the adjacent vertebrae when in a fully rotated, translated or open position, the spine plate can rotate further when the adjacent vertebrae are compressed. If the spine plates are mounted to the adjacent vertebrae when in a fully non rotated, translated or closed position, the spine plates cannot rotate when the adjacent vertebrae are compressed.

The first and second spine plates may optionally include mating ratchet features so that the position of the first and second plates is locked between intervals of translation while the adjacent vertebrae are always compressing on the interbody spacer. The mating ratchet features may be positioned on arms of the first and second spine plates.

In another form, the spinal plate is defined by first and second spine plates or plate portions that are movably retained by the interbody spacer. Such movement may be independent. The spine plates are coupled to the interbody spacer for superior/inferior movement relative thereto. In one form of this embodiment, each spine plate has tangs on both lateral sides of the plate body, each tang of which is movably connected to the interbody spacer. In a static form of the invention, the tangs are rendered immobile so as to prevent translation of either or both of the spine plates.

In all cases, the first and second spine plates each have one, two or more screw holes for accepting a bone screw for fixing the spine plates to the adjacent vertebrae.

BRIEF DESCRIPTION OF THE DRAWINGS

The above mentioned and other features, advantages and/or or objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

Figure 1:
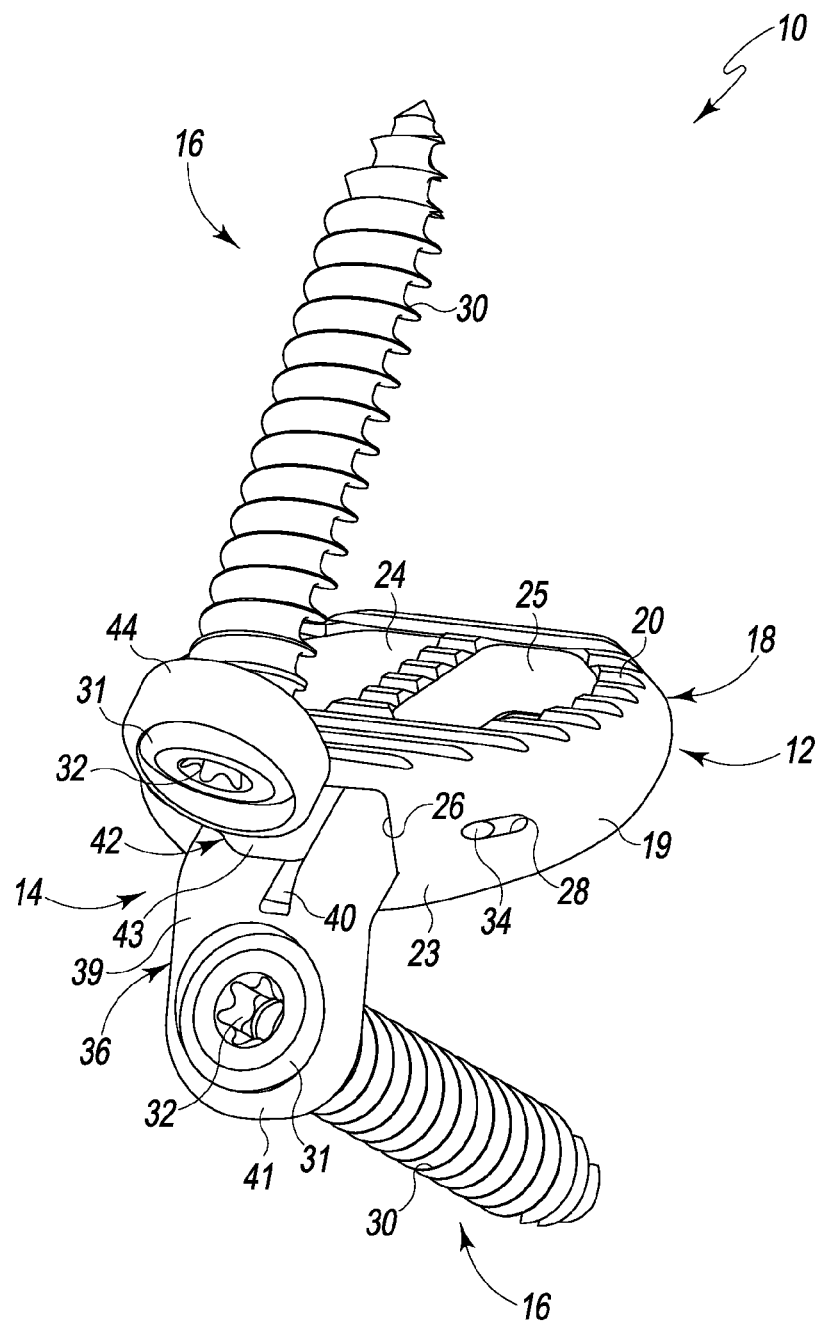
FIG. 1 is a perspective view of an embodiment of a combined spinal interbody and plate fashioned in accordance with the present principles, the spine plate formed as a two-screw alignment/tension spine plate and shown in an open or dynamized position.
Figure 2:
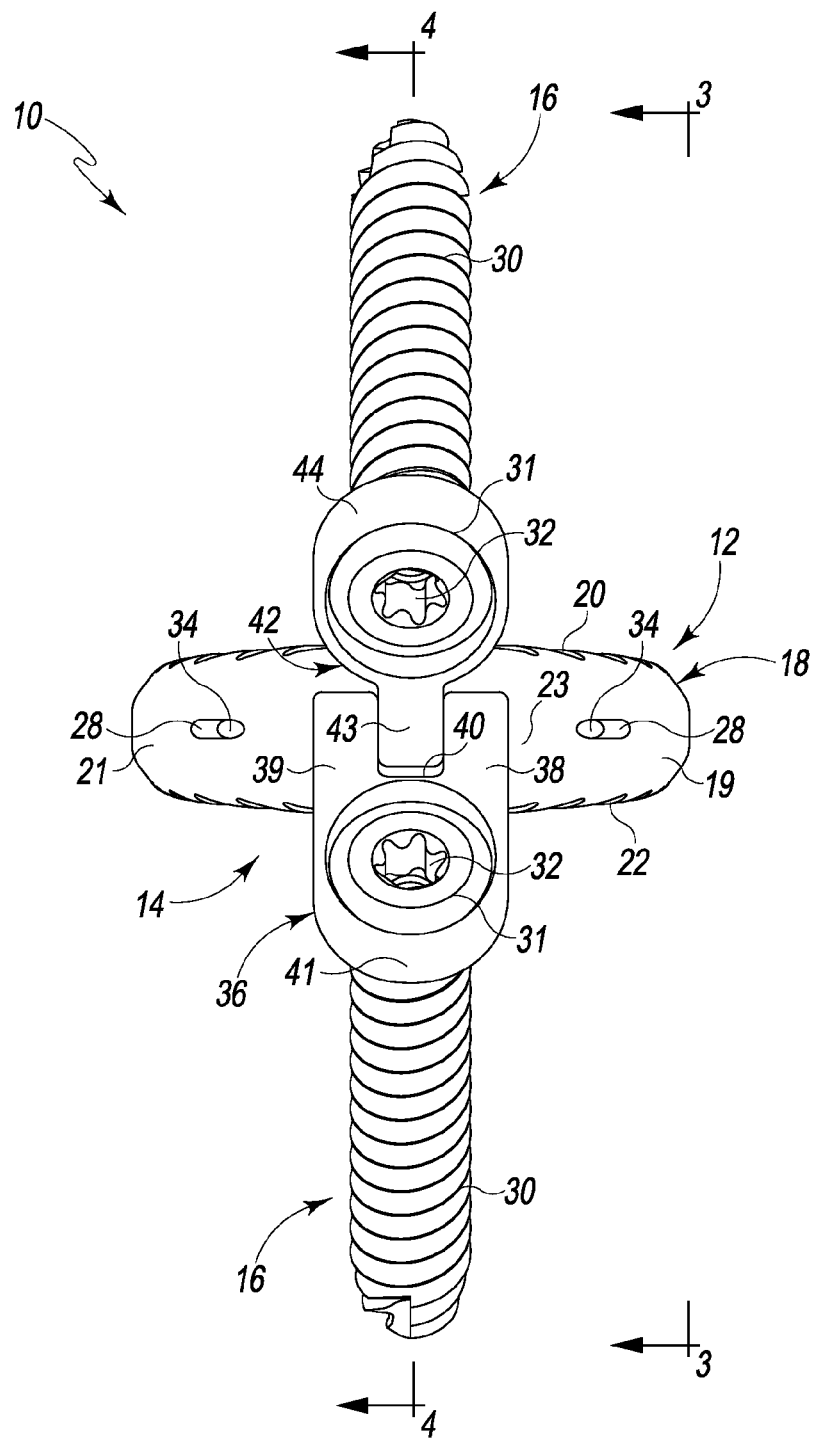
FIG. 2 is a front (anterior) view of the open combined spinal interbody and two-screw alignment/tension spine plate of FIG. 1.

A description of the features, functions and/or configuration of the components depicted in the various figures will now be presented. It should be appreciated that not all of the features of the components of the figures are necessarily described. Some of these non-discussed features, if any, as well as discussed features are inherent from the figures. Other non-discussed features may be inherent in component geometry and/or configuration.

DETAILED DESCRIPTION OF EMBODIMENTS OF THE INVENTION

Referring to FIGS. 1-9, there is depicted various views of an embodiment of a spinal prosthesis comprising a combined spinal interbody and plate fashioned in accordance with the present principles. The present spinal prosthesis may also be described as an intervertebral spinal spacer and spine plate assembly. The present spinal prosthesis may also be described in other manners and/or nomenclatures. The present spinal prosthesis provides stabilization and torsional resistance to promote fusion of adjacent vertebrae of the spine.

The intervertebral spinal spacer and spine plate assembly, generally designated 10 (the "assembly 10"), is a two-screw spine plate embodiment wherein a single screw is used in each adjacent vertebrae for mounting thereof. The assembly 10 is characterized by an intervertebral spinal spacer (intervertebral spacer) 12 and a spine plate 14. The intervertebral spacer 12 is formed of a body 18 that is sized and configured for reception in an intervertebral space between adjacent vertebrae in which a spinal disc was previously situated. The body 18 is thus designed to fit within an intervertebral space. In the present embodiment, the body 18 is generally disc-shaped. It should be appreciated that the body 18 may be configured differently while adhering to the present principles.

The body 18 has a first side 20, a second side 22, a posterior end 27, an anterior end 23, a first lateral side 19 and a second lateral side 21, the nomenclature first and second being arbitrary. The first side 20 may be considered the superior side while the second side 22 may be considered the inferior side. It should be appreciated, however, that the second side may be considered the superior side while the first side may be considered the inferior side. Hereinafter, however, the first side 20 will be considered the superior side while the second side 22 will be considered the inferior side. The body 18 includes first and second cavities 24, 25 that extend from and between the first and second sides 20, 22.

Figure 3:
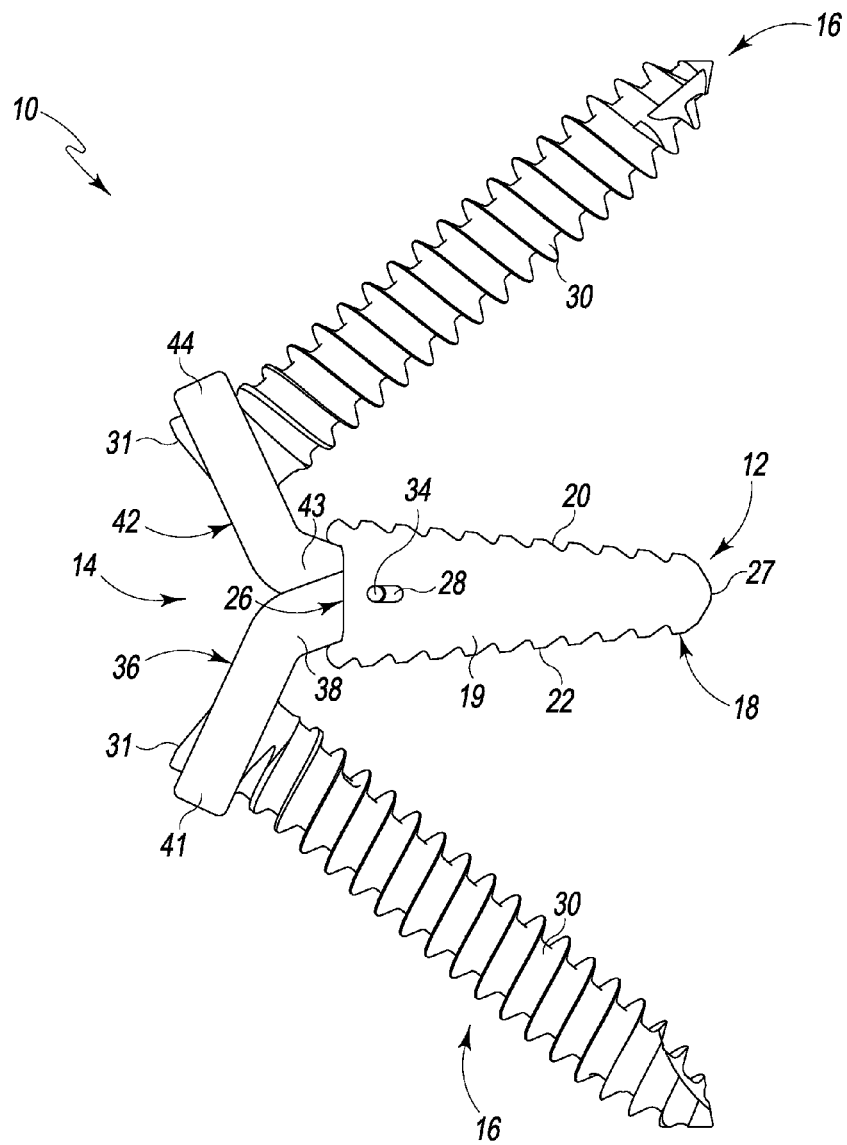
FIG. 3 is a side view of the open combined spinal interbody and two-screw alignment/tension spine plate of FIG. 1 taken along line 3-3 of FIG. 2.
Figure 4:
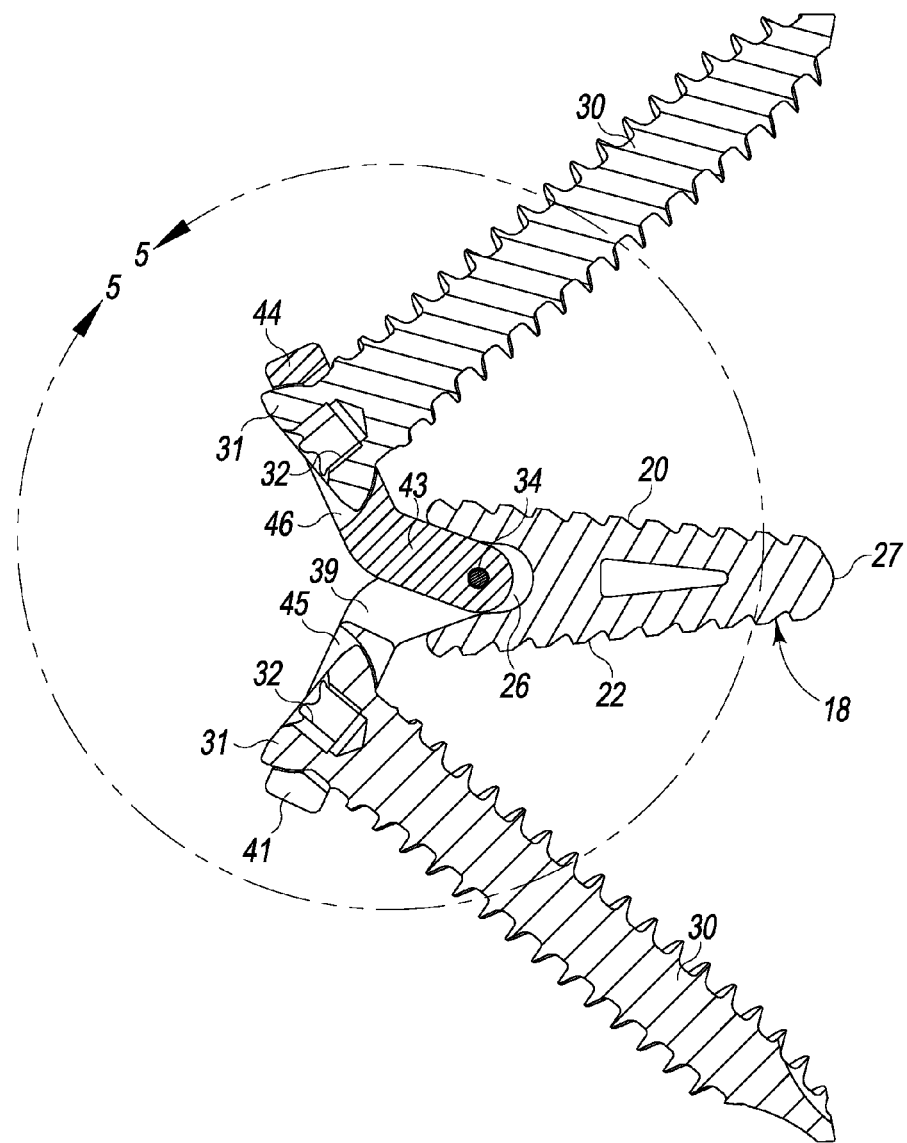
FIG. 4 is a sectional view of the open combined spinal interbody and two-screw alignment/tension spine plate of FIG. 1 taken along line 4-4 of FIG. 2.
Figure 5:
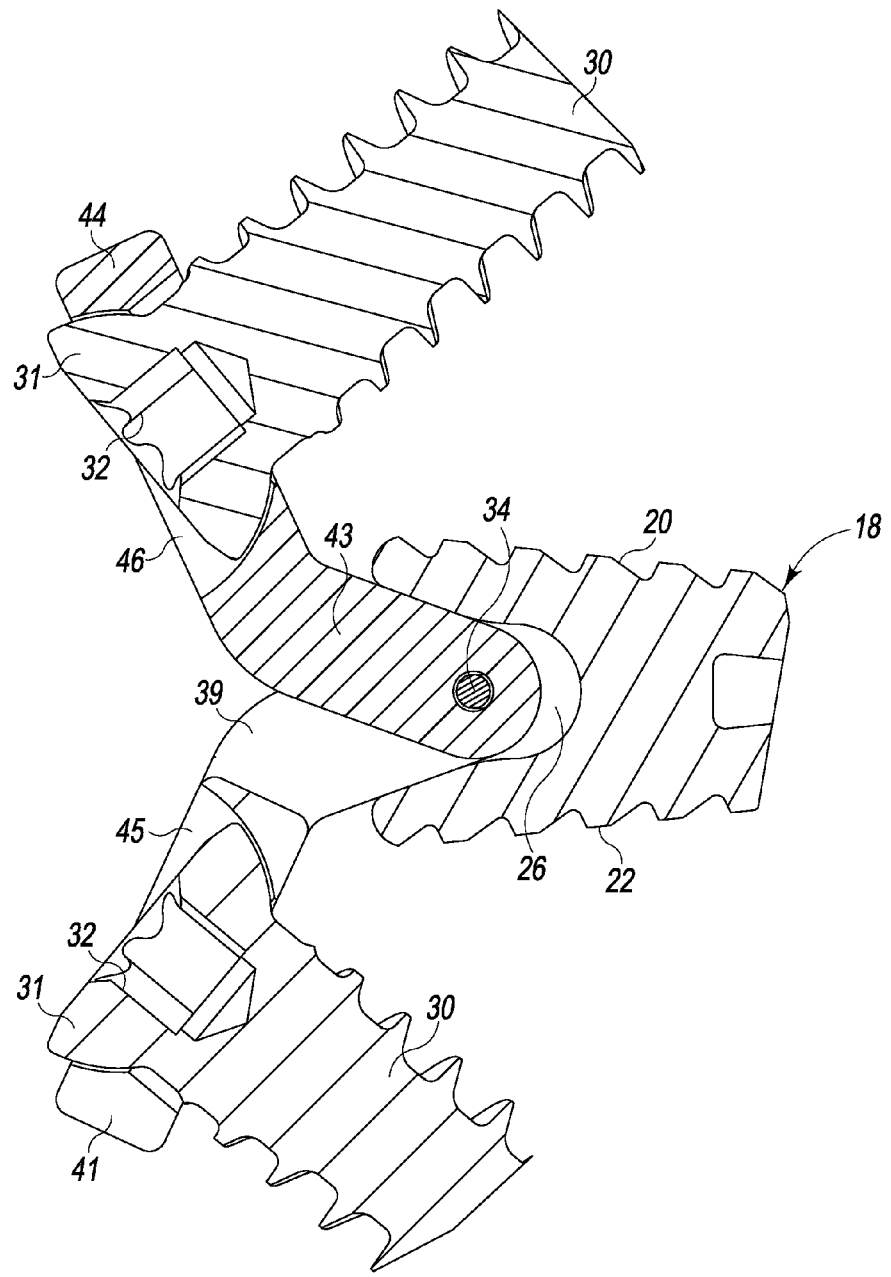
FIG. 5 is an enlarged portion of the sectional view of FIG. 4 taken along circle 5-5 thereof.
Figure 6:
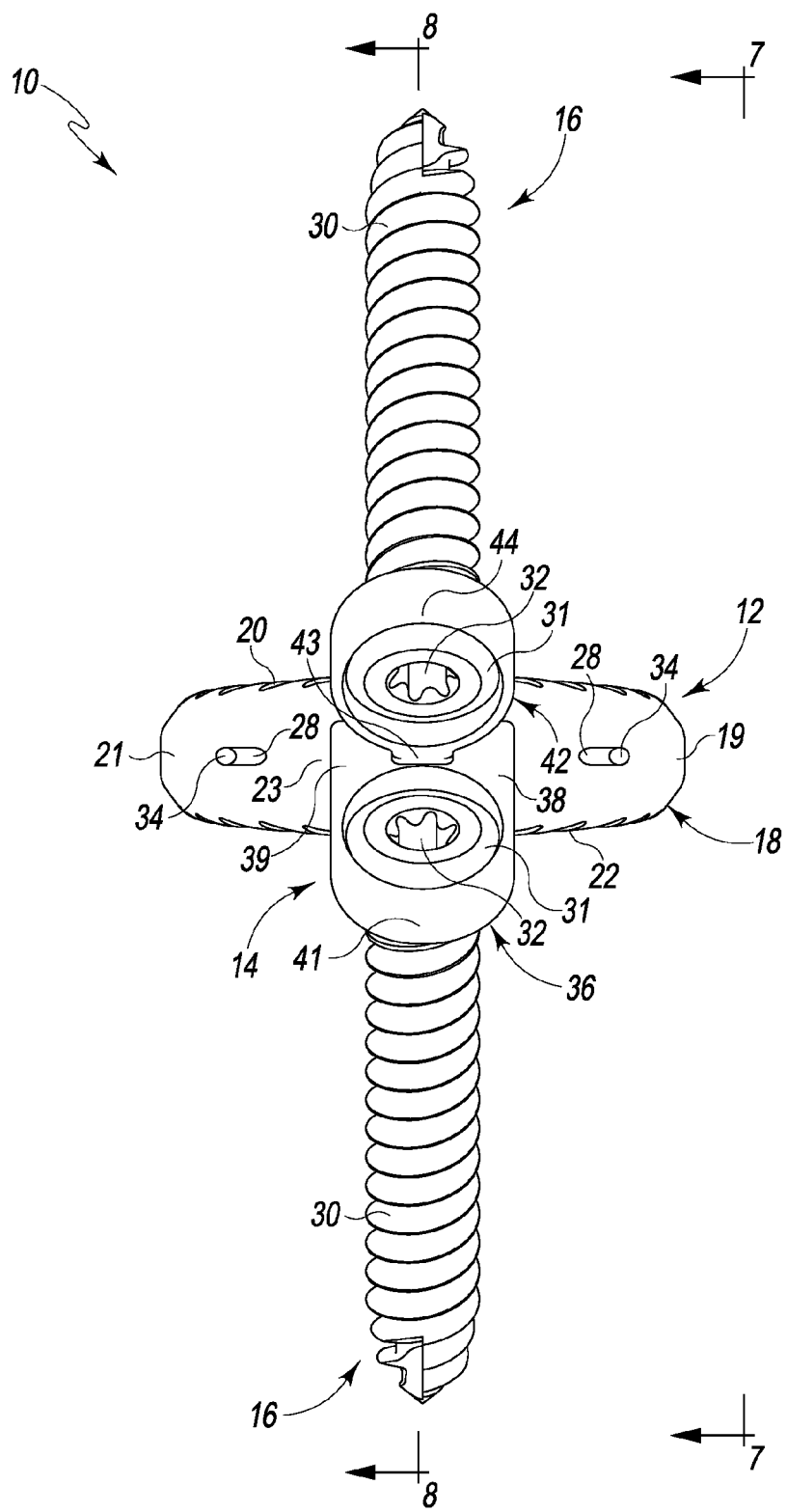
FIG. 6 is a front (anterior) view of the combined spinal interbody and two-screw alignment/tension spine plate of FIG. 1 shown in a closed or un-dynamized position.
Figure 7:
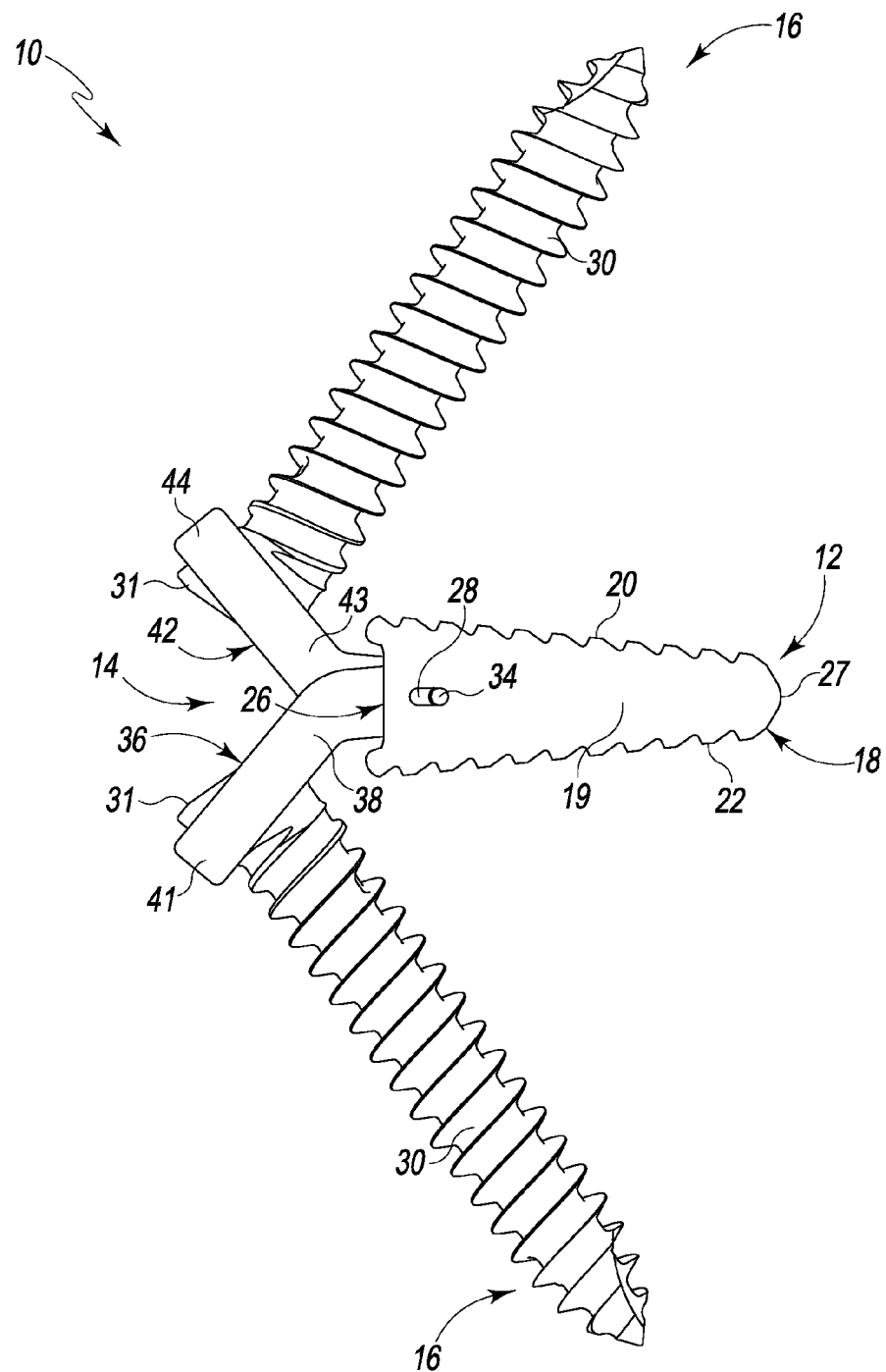
FIG. 7 is a side view of the closed combined spinal interbody and two-screw alignment/tension spine plate of FIG. 6 taken along line 7-7 thereof.
Figure 8:
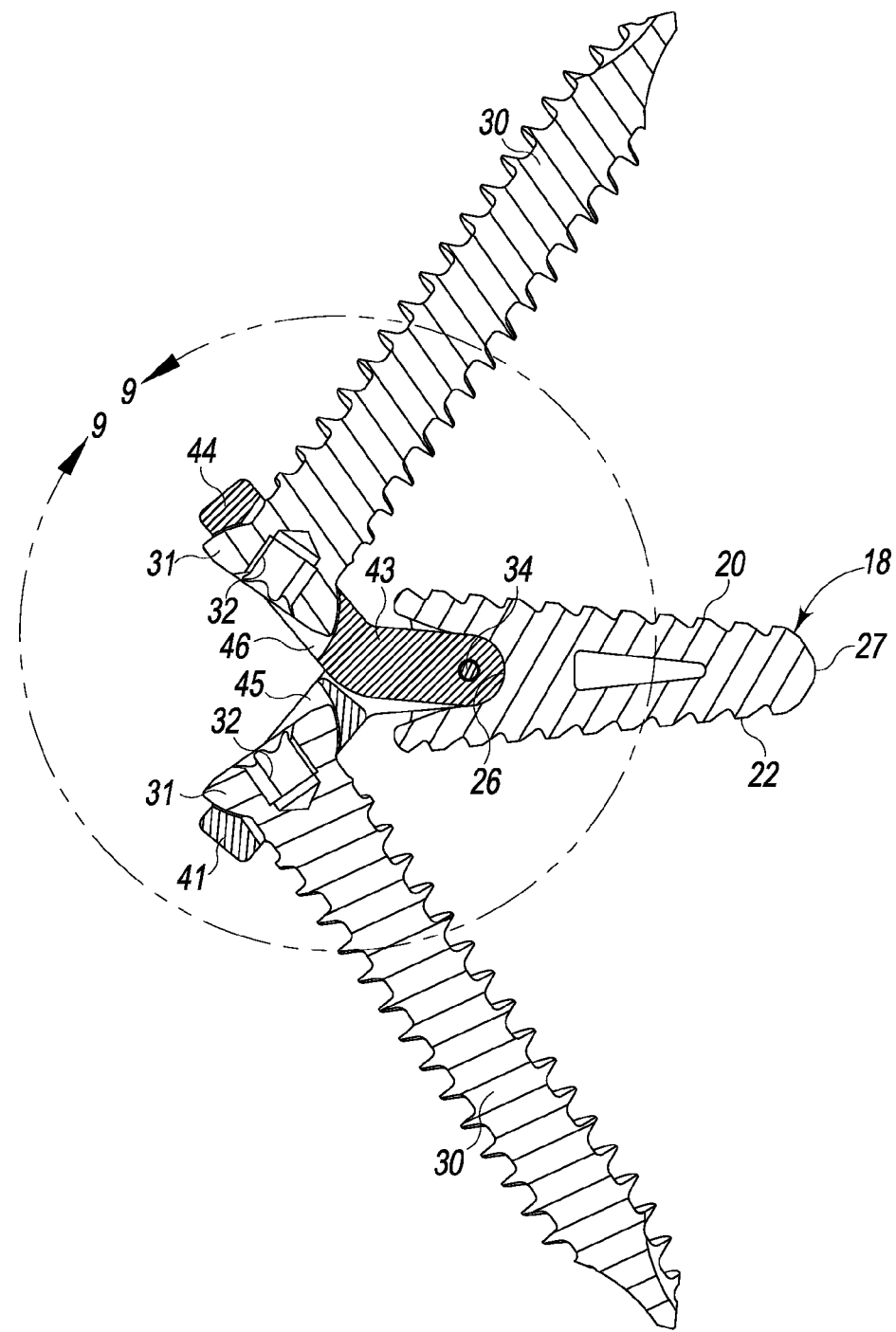
FIG. 8 is a sectional view of the closed combined spinal interbody and two-screw alignment/tension spine plate of FIG. 6 taken along line 8-8 thereof.
Figure 9:
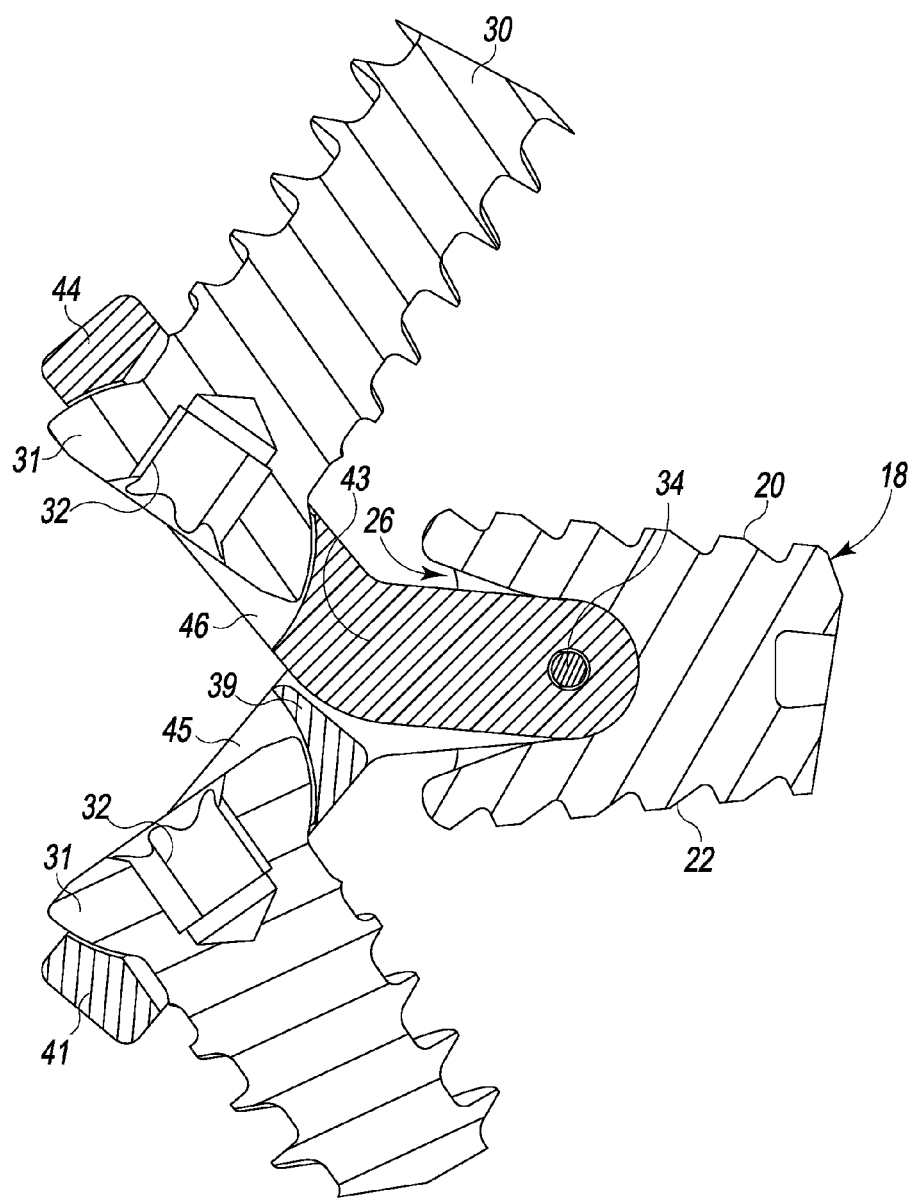
FIG. 9 is an enlarged portion of the sectional view of FIG. 8 taken along circle 9-9 thereof.
Figure 10:
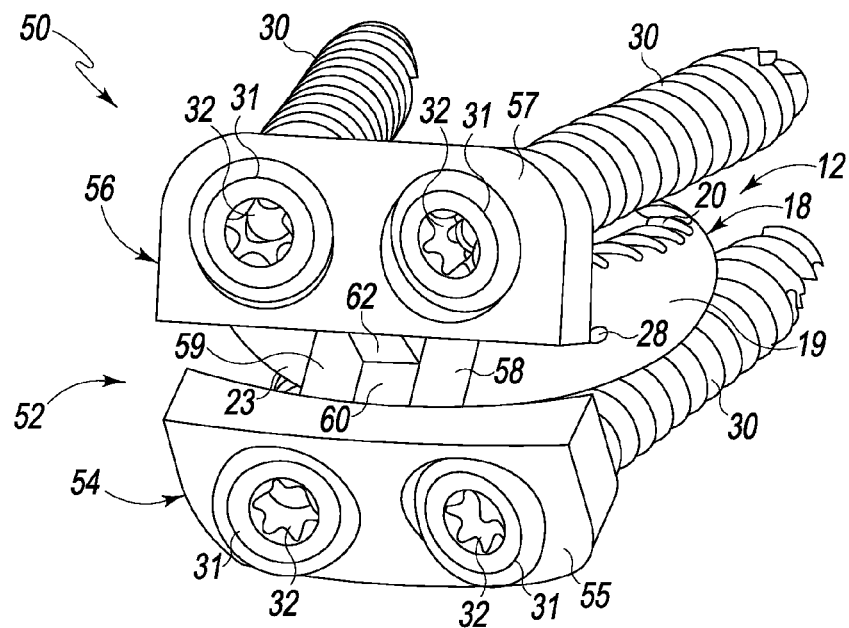
FIG. 10 is a perspective view of an embodiment of a combined spinal interbody and plate fashioned in accordance with the present principles, the spinal plate formed as a four-screw alignment/tension spine plate and shown in an open or dynamized position.
Figure 11:
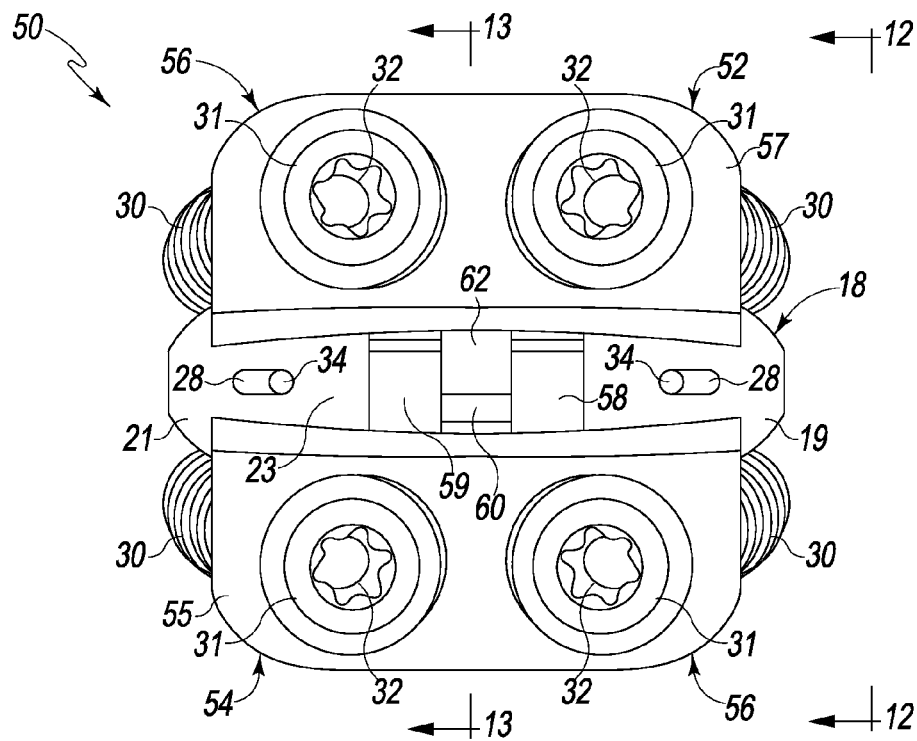
FIG. 11 is a front (anterior) view of the open combined spinal interbody and four-screw alignment/tension spine plate of FIG. 10.
Figure 12:
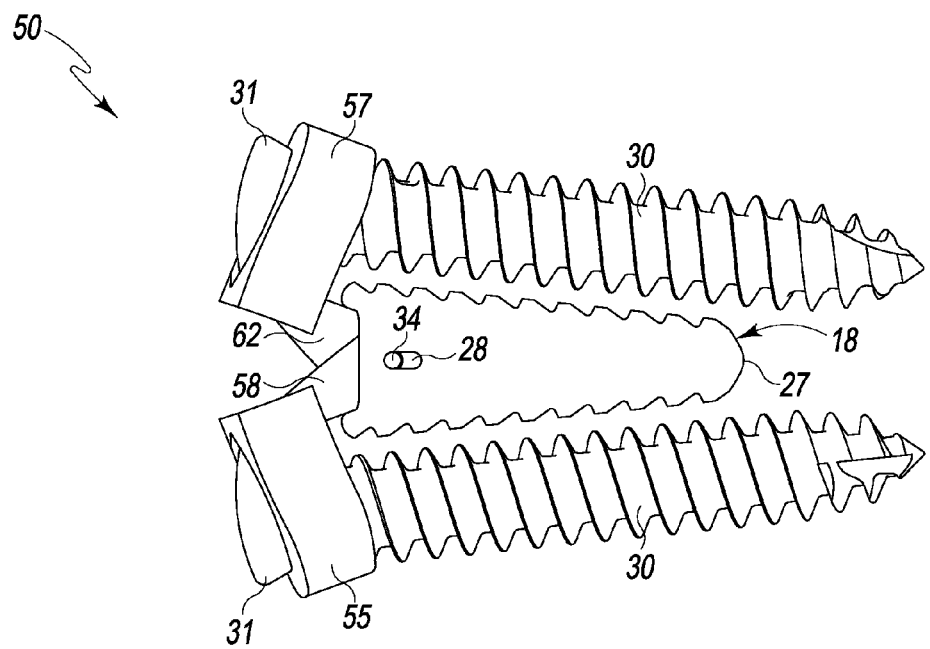
FIG. 12 is a side view of the open combined spinal interbody and four-screw alignment/tension spine plate of FIG. 10 taken along line 12-12 of FIG. 11.
Figure 13:
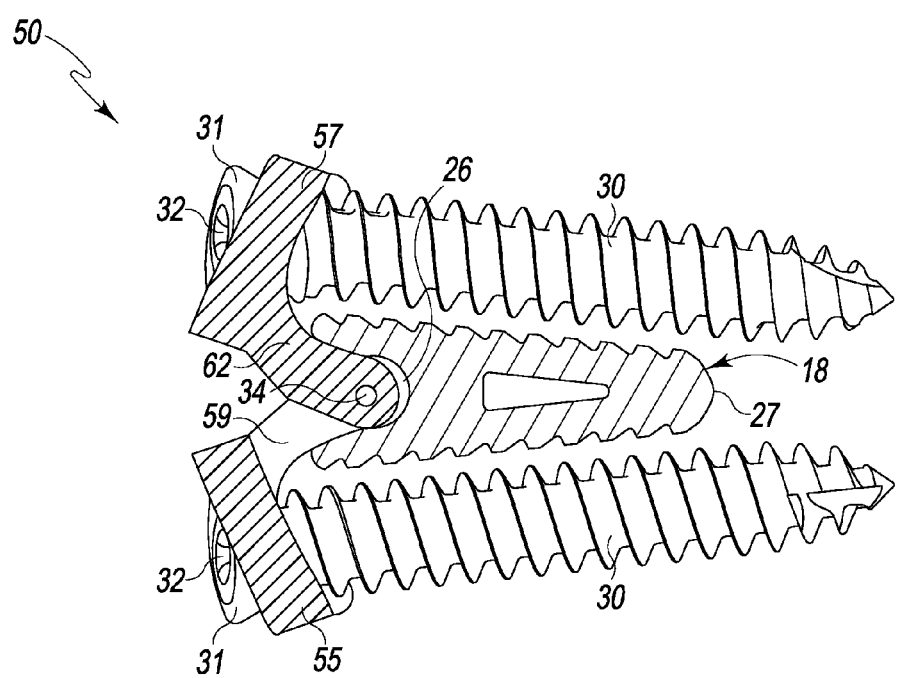
FIG. 13 is a sectional view of the open combined spinal interbody and four-screw alignment/tension spine plate of FIG. 10 taken along line 13-13 of FIG. 11.

As best seen in FIGS. 3 and 4, the first side 20 slopes downwardly from the anterior end 23 to the posterior end 27 of the body 18 while the second side 22 slopes upwardly from the anterior end 23 to the posterior end 27 to define a wedge shape. It should be appreciated, however, that the body 18 may not be necessarily wedge-shaped, but instead have a parallel or reversed wedge-shape configuration. Other configurations are contemplated. The first side 20 has a plurality of teeth that are configured so as to slant or angle in the anterior direction. Likewise, the second side 22 has a plurality of teeth that are configured so as to slant or angle in the anterior direction. When installed in the intervertebral space of adjacent vertebrae from the anterior side to the posterior side, the teeth provide an anti back-out mechanism. The body 18 also includes a bore 28 that extends from and between the first and second lateral sides 19, 21 of the body 18. A pin 34 is disposed in the bore 28 and likewise extends from and between the first and second lateral sides 19, 21 of the body 18. As described in detail below, the pin 34 pivotally holds the spine plate construct 14 and particularly, the first and second spine plate portions 36 and 42 thereof within a cavity 26 of the body 18, the cavity 26 provided in the anterior end 23 of the body 18.

The spine plate 14 is characterized by a first spine plate portion 36 and a second spine plate portion 42, with the nomenclature first and second again being arbitrary. The first spine plate portion 36 has a bone screw boss 41 having a tapered bore 45 that is sized and configured to receive the head 31 of a bone screw 16 and to allow the axial positioning of the threaded shank 30 of the bone screw 16 to be variable relative to the bone screw boss 41. The head 31 of the bone screw 16 is shown with a configured socket 32. The second spine plate portion 42 has a bone screw boss 44 having a tapered bore 46 that is sized and configured to receive the head 31 of a bone screw 16 and to allow the axial positioning of the threaded shank 30 of the bone screw 16 to be variable relative to the bone screw boss 45. It should be appreciated that the bore 46 may be sized and configured for a fixed axial position of the bone screw.

The first spine plate portion 36 has a first angled arm 38 extending from one side of the bone screw boss 41 and a second angled arm 39 extending from another side of the bone screw boss 41. The arms 38 and 39 form forks or tines of the first spine plate portion 36. A slot 40 is thus defined between the first and second angled arms 38, 39. The second spine plate portion 42 has an angled arm 43 extending from a middle of the bone screw boss 44. The spine plate 14 comprises the coupled first and second spine plate portions 36, 42. Particularly, the angled arm 43 of the second spine plate portion 42 extends through the slot 40 between the first and second arms 38, 39 of the first spine plate portion 36 and is pivotally coupled (i.e. hinged) to the first and second arms 38, 39 via the pin 34 (see, e.g. FIGS. 4 and 5). Other manners of providing a pivoting spine plate may be used and are contemplated.

The spine plate 14 is thus received in the intervertebral spacer 12 by the reception of the arms 38, 39 and 43 in the cavity 26 of the intervertebral spacer 12 and retained by the pin 34. The first and second spine plate portions 36, 42 are thus free to rotate about the pin 34 in order to properly position the corresponding bone screw bosses 41, 44 relative to the adjacent vertebrae for securing the plate portions onto the adjacent vertebrae. The slot 34 is sized to allow anterior/posterior movement of the spine plate 14 relative to the intervertebral spacer 12. It should be appreciated however, that the slot 34 may be sized to not allow such movement.

The spinal prosthesis 10 of FIGS. 1-5 is shown in a generally fully extended, translated, rotated, open or dynamized position. In this position, the first and second spine plate portions 36, 42 are pivoted or rotated away from each other the most that they can be rotated while still being associated with the intervertebral spacer 12 (i.e. the first spine plate portion 36 being rotated in the counterclockwise direction with the second spine plate portion 42 being rotated in the clockwise direction the most that the spine plate portions 36 and 42 can rotate).

When installed in this position, the spine plate 14 (the spine plate portions 36 and 42) allow vertebral compression. Particularly, there is movement, compression or dynamization allowed between the spine plate portions and the intervertebral spacer.

In contrast to the position of the spinal prosthesis 10 of FIGS. 1-5, FIGS. 6-9 depict the spinal prosthesis 10 in a generally fully compressed, non-translated, non-rotated, closed or un-dynamized position. In this position, the first and second spine plate portions 36, 42 are pivoted or rotated toward each other the most that they can be rotated while still being associated with the intervertebral spacer 12 (i.e. the first spine plate portion 36 being rotated in the counterclockwise direction with the second spine plate portion 42 being rotated in the clockwise direction the most that the spine plate portions 36 and 42 can rotate).

When installed in this position, the spine plate 14 (the spine plate portions 36 and 42) does not allow vertebral compression. Particularly, there is no further compression movement or dynamization allowed between the spine plate portions (i.e. they cannot close any more relative to one another).

Referring to FIGS. 10-13, there is depicted various views of an embodiment of a spinal prosthesis comprising a combined spinal interbody and plate fashioned in accordance with the present principles. The present spinal prosthesis may also be described as an intervertebral spinal spacer and spine plate assembly. The present spinal prosthesis may also be described in other manners and/or nomenclatures. The present spinal prosthesis provides stabilization and torsional resistance to promote fusion of adjacent vertebrae of the spine.

The intervertebral spinal spacer and spine plate assembly, generally designated 50 (the "assembly 50"), is a four-screw spine plate embodiment wherein two screws are used in each adjacent vertebrae for mounting thereof. The assembly 50 is characterized by an intervertebral spinal spacer (intervertebral spacer) 12 and a spine plate 52. The intervertebral spacer 12 is the same as that described above with respect to the embodiment of FIGS. 1-9 and thus reference is made thereto for an understanding thereof.

The spine plate 52 is characterized by a first spine plate portion 54 and a second spine plate portion 56, with the nomenclature first and second again being arbitrary. The first spine plate portion 54 is defined by a plate 55 having two bone screw bosses each having a tapered bore that is sized and configured to receive the head 31 of a bone screw 16 and to allow the axial positioning of the threaded shank 30 of the bone screw 16 to be variable relative to the bone screw bosses and thus the plate 55 (not necessarily variable; can also be fixed). The second spine plate portion 56 is defined by a plate 57 having two bone screw bosses each having a tapered bore that is sized and configured to receive the head 31 of a bone screw 16 and to allow the axial positioning of the threaded shank 30 of the bone screw 16 to be variable relative to the bone screw bosses and thus the plate 57.

The first spine plate portion 54 has a first angled arm 58 extending from one side of the plate 55 and a second angled arm 59 extending from another side of the plate 55; the arms 58, 59 forming forks or tines. A slot 60 is defined between the first and second angled arms 58, 59. The second spine plate portion 56 has an angled arm 62 extending from a middle of the plate 57. The spine plate 14 comprises the coupled first and second spine plate portions 54, 56. Particularly, the angled arm 62 of the second spine plate portion 56 extends through the slot 60 between the first and second arms 58, 59 of the first spine plate portion 54 and is pivotally coupled (i.e. hinged) to the first and second arms 58, 59 via the pin 34 (see, e.g. FIG. 13).

The spine plate construct 52 is thus received in the intervertebral spacer 12 by the reception of the arms 58, 59 and 62 in the cavity 26 of the intervertebral spacer 12 and retained by the pin 34. The first and second spine plate portions 54, 56 are thus free to rotate about the pin 34 in order to properly position the corresponding bone screw bosses/plates 55, 57 relative to the adjacent vertebrae for securing the plate portions onto the adjacent vertebrae. The slot 34 is sized to allow anterior/posterior movement of the spine plate 52 relative to the intervertebral spacer 12. It should be appreciated however, that the slot 34 may be sized to not allow such movement.

The spinal prosthesis 50 of FIGS. 10-13 is shown in a generally fully extended, translated, rotated, open or dynamized position. In this position, the first and second spine plate portions 54, 56 are pivoted or rotated away from each other the most that they can be rotated while still being associated with the intervertebral spacer 12 (i.e. the first spine plate portion 54 being rotated in the counterclockwise direction with the second spine plate portion 56 being rotated in the clockwise direction the most that the spine plate portions 54 and 56 can rotate).

When installed in this position, the spine plate 52 (the spine plate portions 54 and 56) allow vertebral compression. Particularly, there is movement, compression or dynamization allowed between the spine plate portions and the intervertebral spacer.

In another embodiment of the design, two plates are attached to the intervertebral spacer via two pins that extend from the superior to inferior surfaces of the spacer. The plates are allowed to translate along the pins or dynamize to accommodate subsidence within the disc space. In the form shown, the screws are contained within disc space and can be screwed into the superior and inferior faces of the vertebral bodies. In another form, the screws can be screwed into anterior faces of the vertebral bodies.

Figure 14:
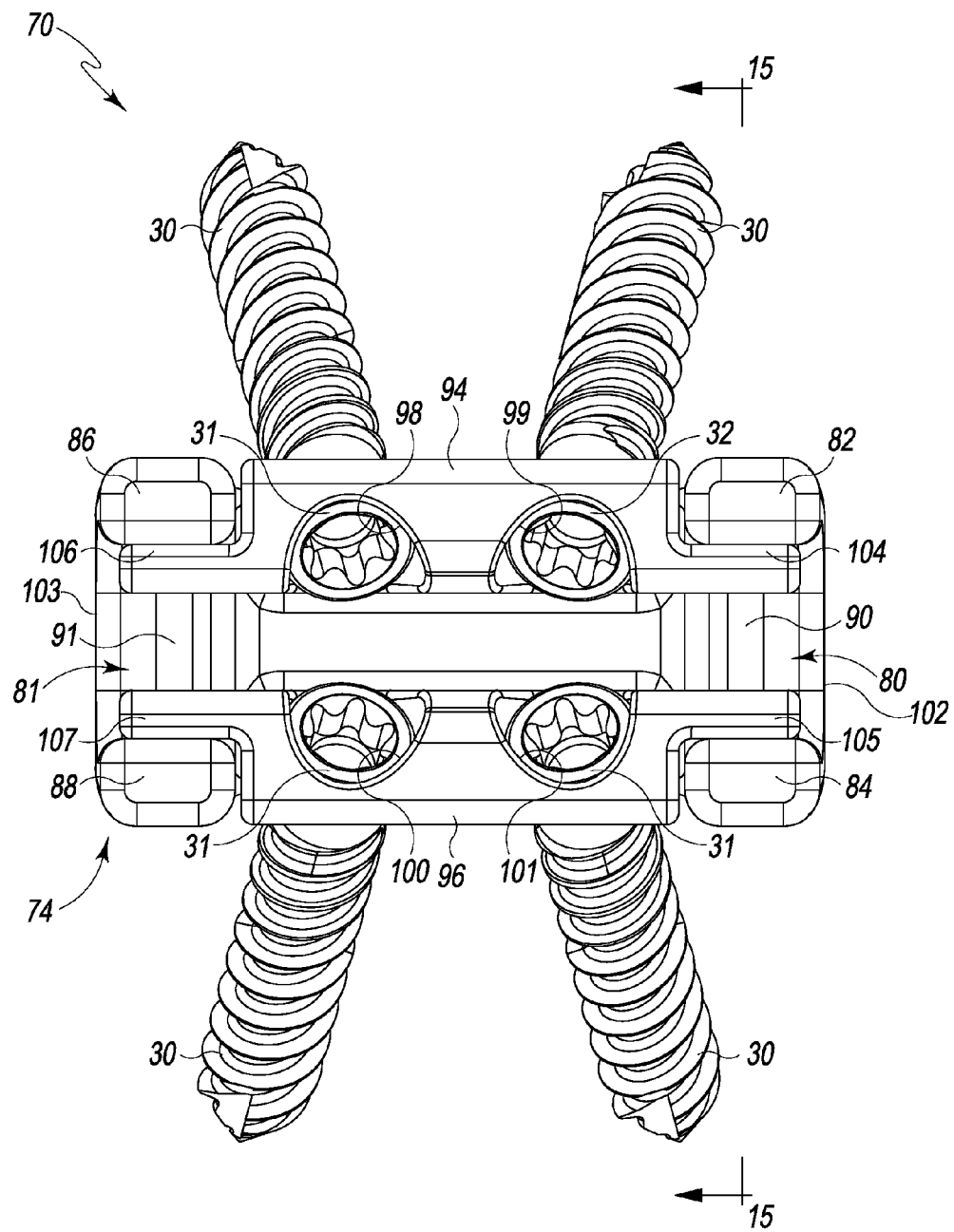
FIG. 14 is a front (anterior) view of an embodiment of another combined spinal interbody and plate fashioned in accordance with the present principles, the spinal plate formed as a four-screw alignment/tension spine plate and shown in an open or dynamized position.
Figure 15:
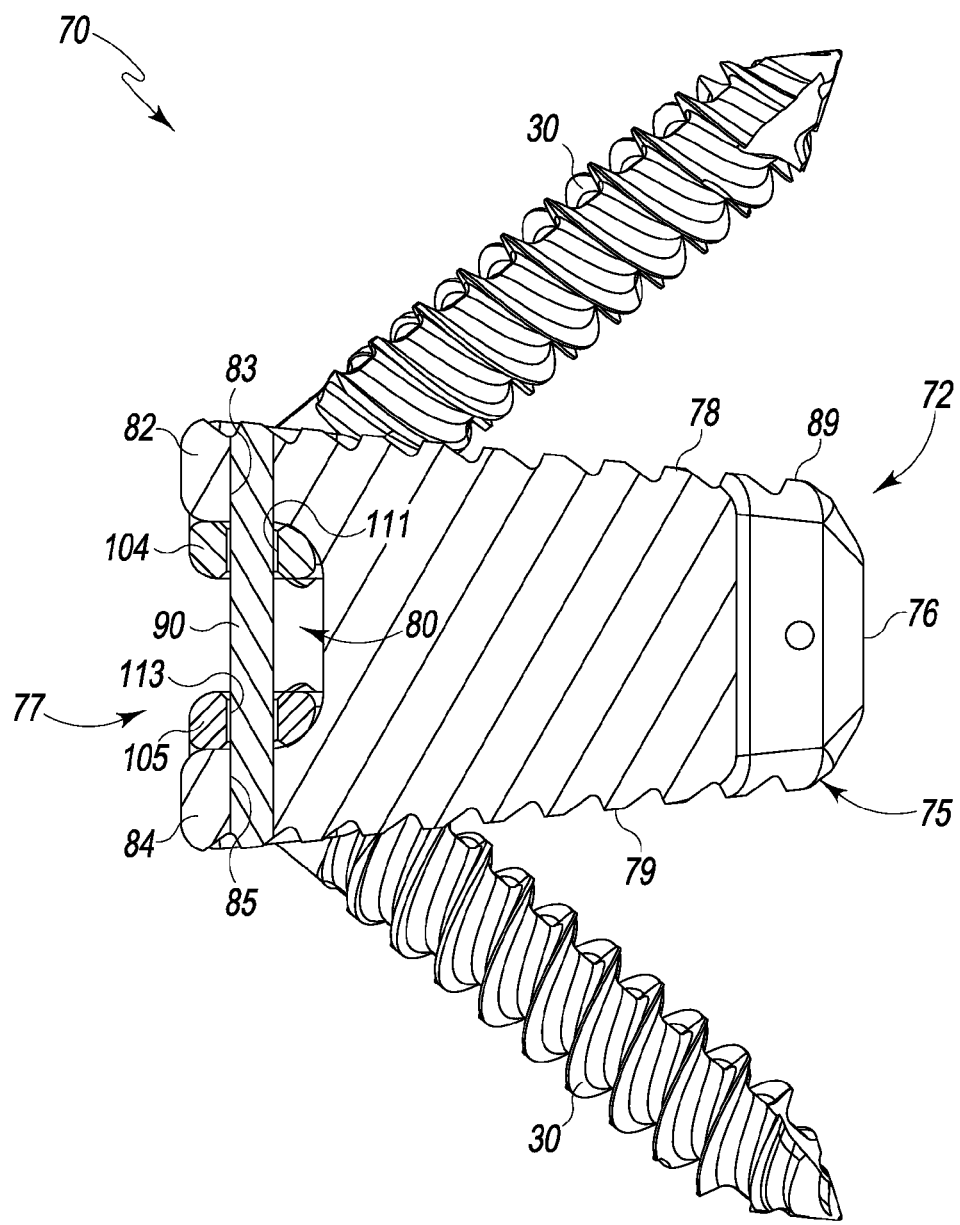
FIG. 15 is a side view of the open combined spinal interbody and four-screw alignment/tension spine plate of FIG. 14 taken along line 15-15 of FIG. 14.
Figure 16:
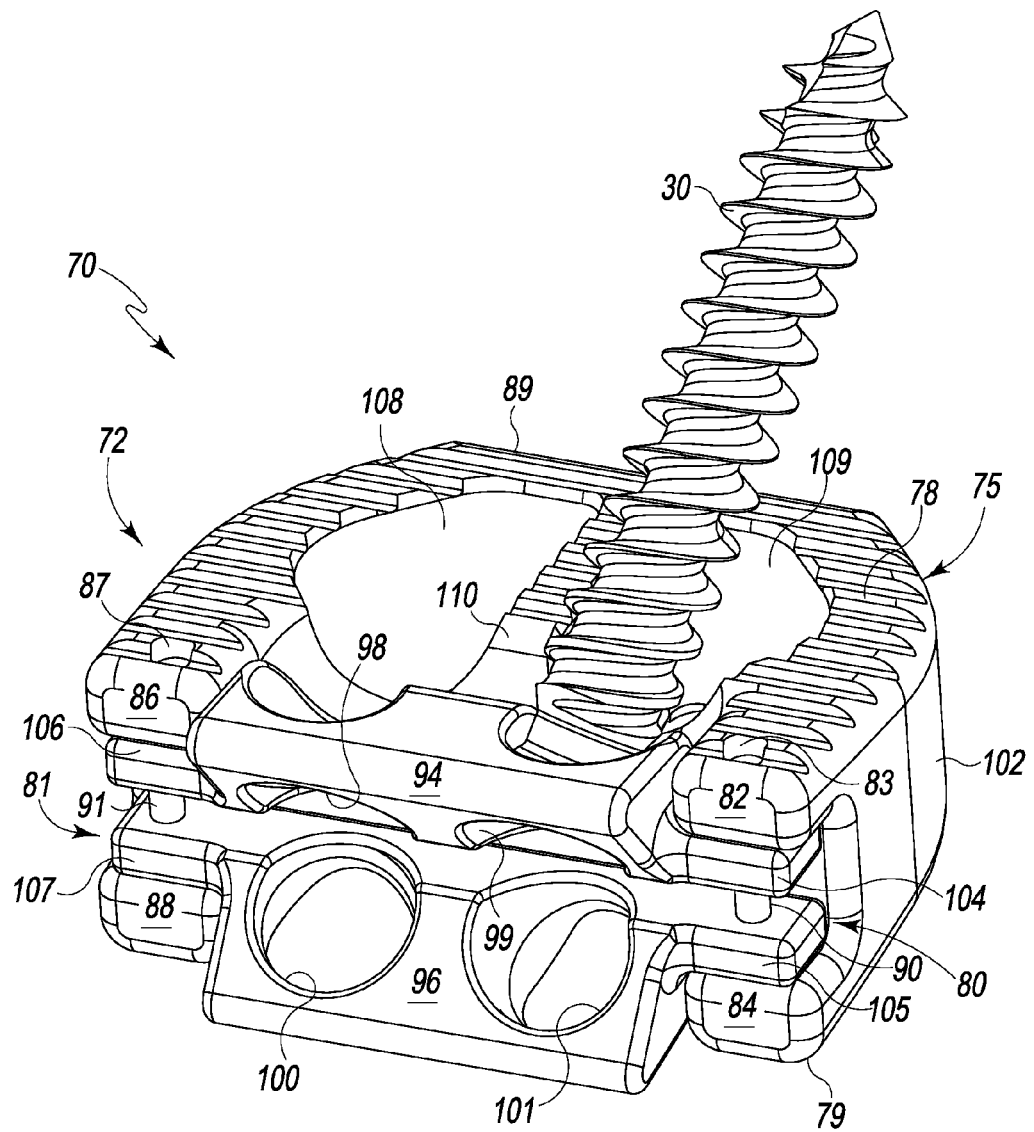
FIG. 16 is a perspective view of the open combined spinal interbody and four-screw alignment/tension spine plate of FIG. 14.
Figure 17:
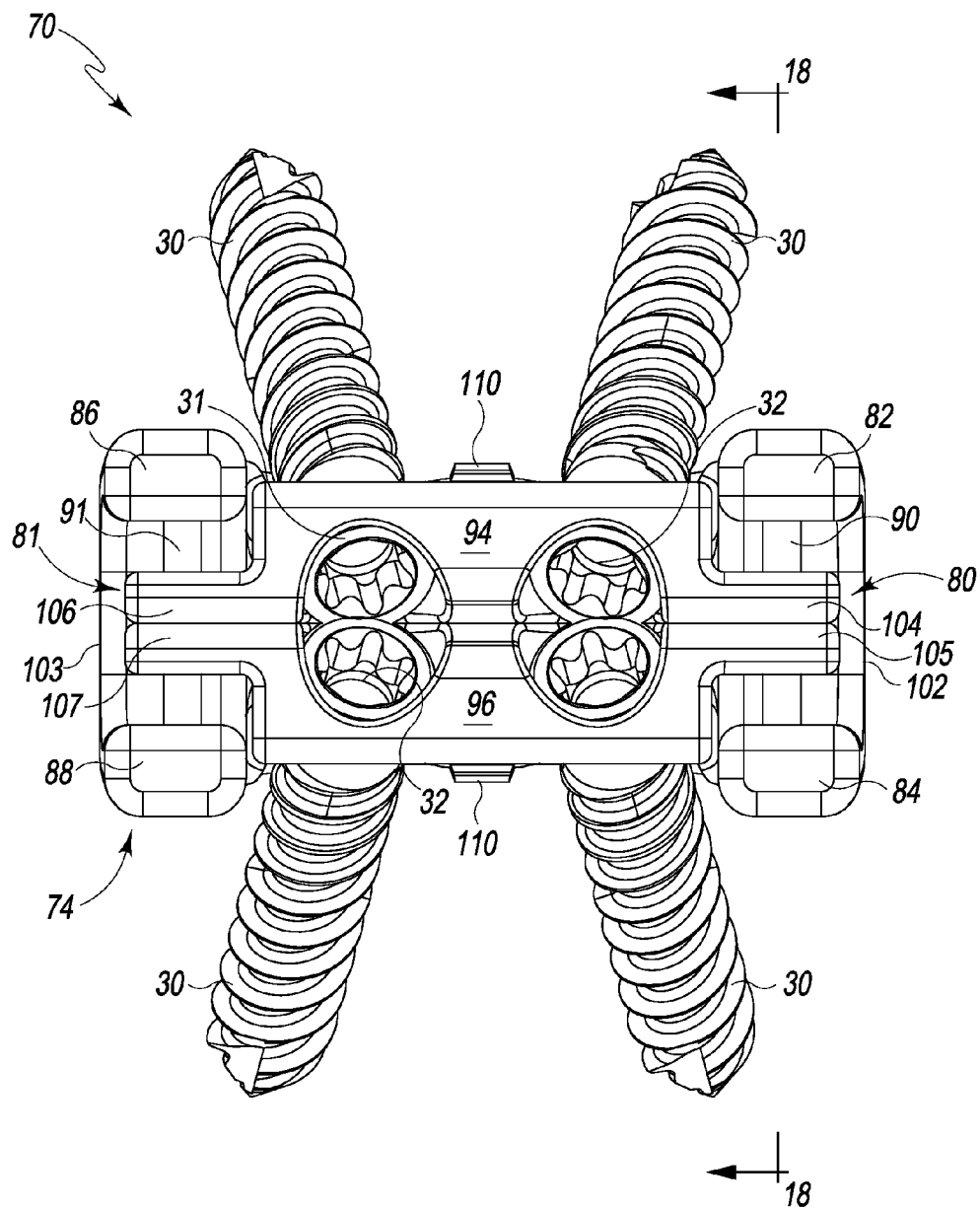
FIG. 17 is a front (anterior) view of the combined spinal interbody and four-screw alignment/tension spine plate of FIGS. 14-16 but shown in a closed or un-dynamized position.
Figure 18:
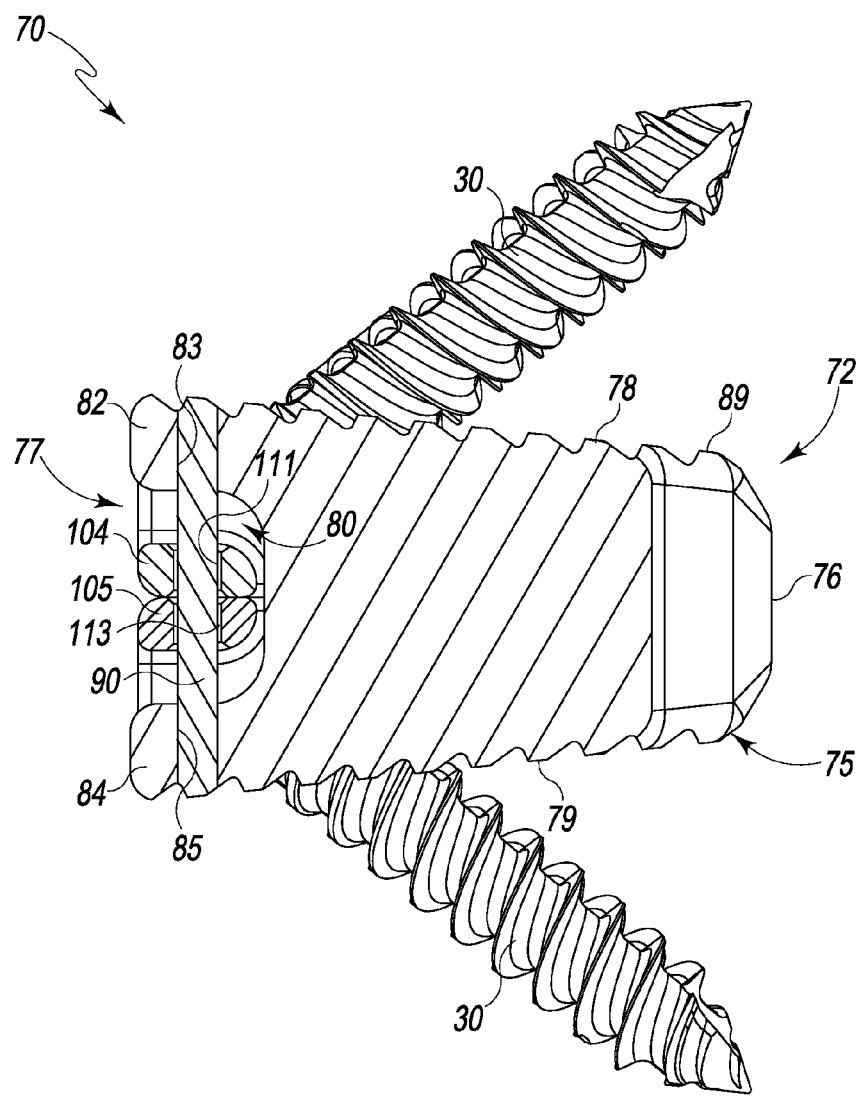
FIG. 18 is a side view of the closed combined spinal interbody and four-screw alignment/tension spine plate of FIG. 17 taken along line 18-18 of FIG. 17.
Figure 19:
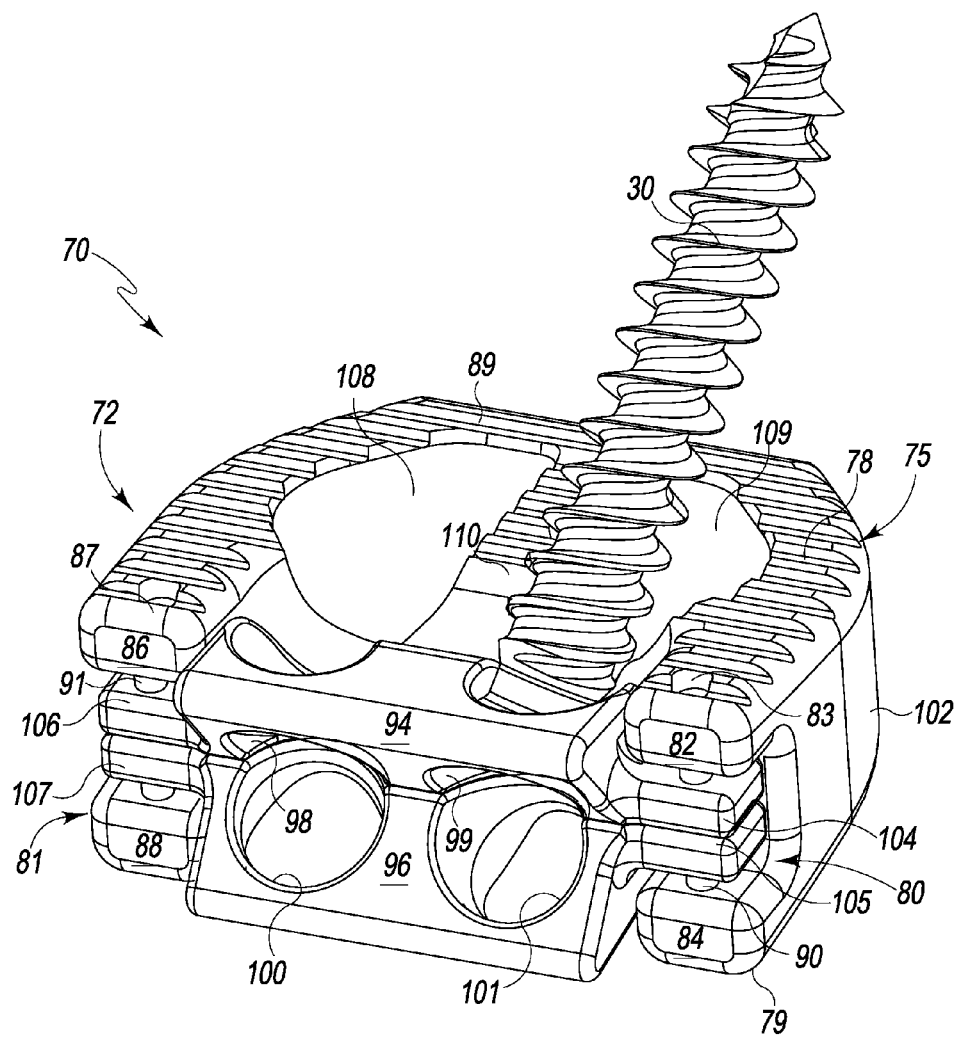
FIG. 19 is a perspective view of the closed compressed combined spinal interbody and four-screw alignment/tension spine plate of FIG. 17.

Referring now to FIGS. 14-16, there is depicted various views of another embodiment of a spinal prosthesis comprising a combined spinal interbody and plate fashioned in accordance with the present principles. The present spinal prosthesis may also be described as an intervertebral spacer and spine plate assembly. The present spinal prosthesis may also be described in other manners and/or nomenclatures. The present spinal prosthesis provides stabilization and torsional resistance to promote fusion of adjacent vertebrae of the spine.

The interbody and spine plate assembly, generally designated 70 (the "assembly 70"), is a four-screw spine plate embodiment wherein two screws are used in each adjacent vertebrae for mounting thereof. The assembly 70 is characterized by an interbody 72 and a spine plate 74. The interbody 72 is formed of a body 75 that is sized and configured for reception in an interbody space. The body 75 is thus designed to fit within an interbody space. In the present embodiment, the body 75 is generally D-shaped or semi disc-shaped. It should be appreciated that the body 75 may be configured differently while adhering to the present principles.

The body 75 has a first side 78, a second side 79, a posterior end 76, an anterior end 77, a first lateral side 102 and a second lateral side 103, the nomenclature first and second being arbitrary. The first side 78 may be considered the superior side while the second side 79 may be considered the inferior side. It should be appreciated, however, that the second side may be considered the superior side while the first side may be considered the inferior side. Hereinafter, however, the first side 78 will be considered the superior side while the second side 79 will be considered the inferior side. The body 75 includes first and second cavities 108, 109 that extend from and between the first and second sides 78, 79.

As best seen in FIG. 15, the first side 78 slopes slightly downwardly from the anterior end 77 to the posterior end 76 of the body 75 while the second side 79 slopes slightly upwardly from the anterior end 77 to the posterior end 76 to define a wedge shape. It should be appreciated, however, that the body 75 may not be necessarily wedge-shaped, but instead have a parallel or reversed wedge-shape configuration. Other configurations are contemplated. The first side 78 has a plurality of teeth that are configured so as to slant or angle in the anterior direction. Likewise, the second side 79 has a plurality of teeth that are configured so as to slant or angle in the anterior direction. When installed in the intervertebral space of adjacent vertebrae from the anterior side to the posterior side, the teeth provide an anti back-out mechanism.

The body 75 also includes a first upper flange 82 that extends in the posterior direction from the first lateral side 102 of the body 75 and a first lower flange 84 that extends in the posterior direction from the first lateral side 102 of the body 75. A vertical bore 83 extends through the first upper flange 82 while a vertical bore 85 extends through the first lower flange 84. A pin, dowel, rod or the like 90 extends through the first upper flange bore 83 and the first lower flange bore 85.

The body 75 further includes a second upper flange 86 that extends in the posterior direction from the second lateral side 103 of the body 75 and a second lower flange 88 that extends in the posterior direction from the second lateral side 103 of the body 75. A vertical bore 87 extends through the second upper flange 86 while a vertical bore (not seen) extends through the second lower flange 88. A pin, dowel, rod or the like 91 extends through the second upper flange bore 86 and the second lower flange bore (not seen).

A space 80 is defined between the first upper flange 82 and the first lower flange 84. The space 80 provides an area of translation for one side of the spine plate 74. A space 81 is defined between the second upper flange 86 and the second lower flange 88. The space 81 provides an area of translation for another side of the spine plate 74. In this manner, the spine plate 74 can provide for dynamization.

The spine plate 74 is characterized by a first spine plate portion 94 and a second spine plate portion 96, with the nomenclature first and second again being arbitrary. The first spine plate portion 94 has a first configured bone screw bore 98 that is sized and configured to receive the head 31 of a bone screw 16 and to allow the axial positioning of the threaded shank 30 of the bone screw 16 to be variable relative to the bone screw bore 98. The first spine plate portion 94 has a second configured bone screw bore 99 that is sized and configured to receive the head 31 of a bone screw 16 and to allow the axial positioning of the threaded shank 30 of the bone screw 16 to be variable relative to the bone screw bore 98. It should be appreciated that the bone screw bores 98, 99 may be configured to provide a fixed angle and/or positioning of the bone screw 16 therein.

The second spine plate portion 96 has a first configured bone screw bore 100 that is sized and configured to receive the head 31 of a bone screw 16 and to allow the axial positioning of the threaded shank 30 of the bone screw 16 to be variable relative to the bone screw bore 100. The second spine plate portion 96 has a second configured bone screw bore 101 that is sized and configured to receive the head 31 of a bone screw 16 and to allow the axial positioning of the threaded shank 30 of the bone screw 16 to be variable relative to the bone screw bore 101. It should be appreciated that the bone screw bores 100, 101 may be configured to provide a fixed angle and/or positioning of the bone screw 16 therein.

The first spine plate portion 94 has a first tang 104 on a first lateral side thereof (proximate the lateral side 102 of the body 75) and a second tang 106 on a second lateral side thereof (proximate the lateral side 103 of the body 75). The first tang 104 includes a bore 111 that is sized to fit about pin 90. The second tang 106 includes a bore therein (not seen) that is sized to fit about the pin 91. In this manner, the first plate portion 94 may translate, move or dynamize in the superior/inferior direction.

The second spine plate portion 96 has a first tang 105 on a first lateral side thereof (proximate the lateral side 102 of the body 75) and a second tang 107 on a second lateral side thereof (proximate the lateral side 103 of the body 75). The first tang 105 includes a bore 113 that is sized to fit about pin 90. The second tang 106 includes a bore therein (not seen) that is sized to fit about the pin 91. In this manner, the second plate portion 96 may translate, move or dynamize in the superior/inferior direction in the same manner as first plate portion 94.

The spine plate 74 is thus retained by the interbody 72 through capture of the tangs 104, 105, 106, 107 by the pins 90, 91. The first and second spine plate portions 64, 96 are thus free to move or translate on/along the length of the pins 90, 91 in the superior/inferior direction in order to properly position the corresponding bone screw bosses 98, 99, 100, 101 relative to the adjacent vertebrae for securing the plate portions onto the adjacent vertebrae. Each spine plate portion 94, 96 has an independent fully open, extended, moved, translated or un-dynamized position such as depicted in the figures when the tangs 104, 105, 106, 107 are closest the respective flanges 82, 84, 86, 88 of the body 75.

The spinal prosthesis 70 of FIGS. 14-16 is thus shown in a generally fully extended, translated, moved, open or dynamized position. In this position, both of the first and second spine plate portions 94, 96 are translated away from each other the most axial distance that they can. When installed in this position, the spine plate 74 (the spine plate portions 94 and 96) allow vertebral compression. Particularly, there is movement, compression or dynamization allowed between the spine plate portions.

In contrast to the position of the spinal prosthesis 70 of FIGS. 14-16, FIGS. 17-19 depict the spinal prosthesis 70 in a generally fully compressed, non-translated, non-moved, closed or un-dynamized position. In this position, the first and second spine plate portions 94, 96 are translated toward each other the most that they can be moved.

When installed in this position, the spine plate portions 94, 96 do not allow vertebral compression; therefore, the interbody 52 takes more of the load relative to the spine plate 74. Particularly, there is no further compression movement or dynamization allowed between the spine plate portions and the interbody (i.e. they can spread out relative to one another).

FIGS. 6-9 depict the spinal prosthesis 10 in a generally fully compressed, non-translated, non-rotated, closed or un-dynamized position. In this position, the first and second spine plate portions 36, 42 are pivoted or rotated toward each other the most that they can be rotated while still being associated with the intervertebral spacer 12 (i.e. the first spine plate portion 36 being rotated in the counterclockwise direction with the second spine plate portion 42 being rotated in the clockwise direction the most that the spine plate portions 36 and 42 can rotate).

When installed in this position, the spine plate 14 (the spine plate portions 36 and 42) does not allow vertebral compression. Particularly, there is no further compression movement or dynamization allowed between the spine plate portions (i.e. they cannot close any more relative to one another).

Figure 20:
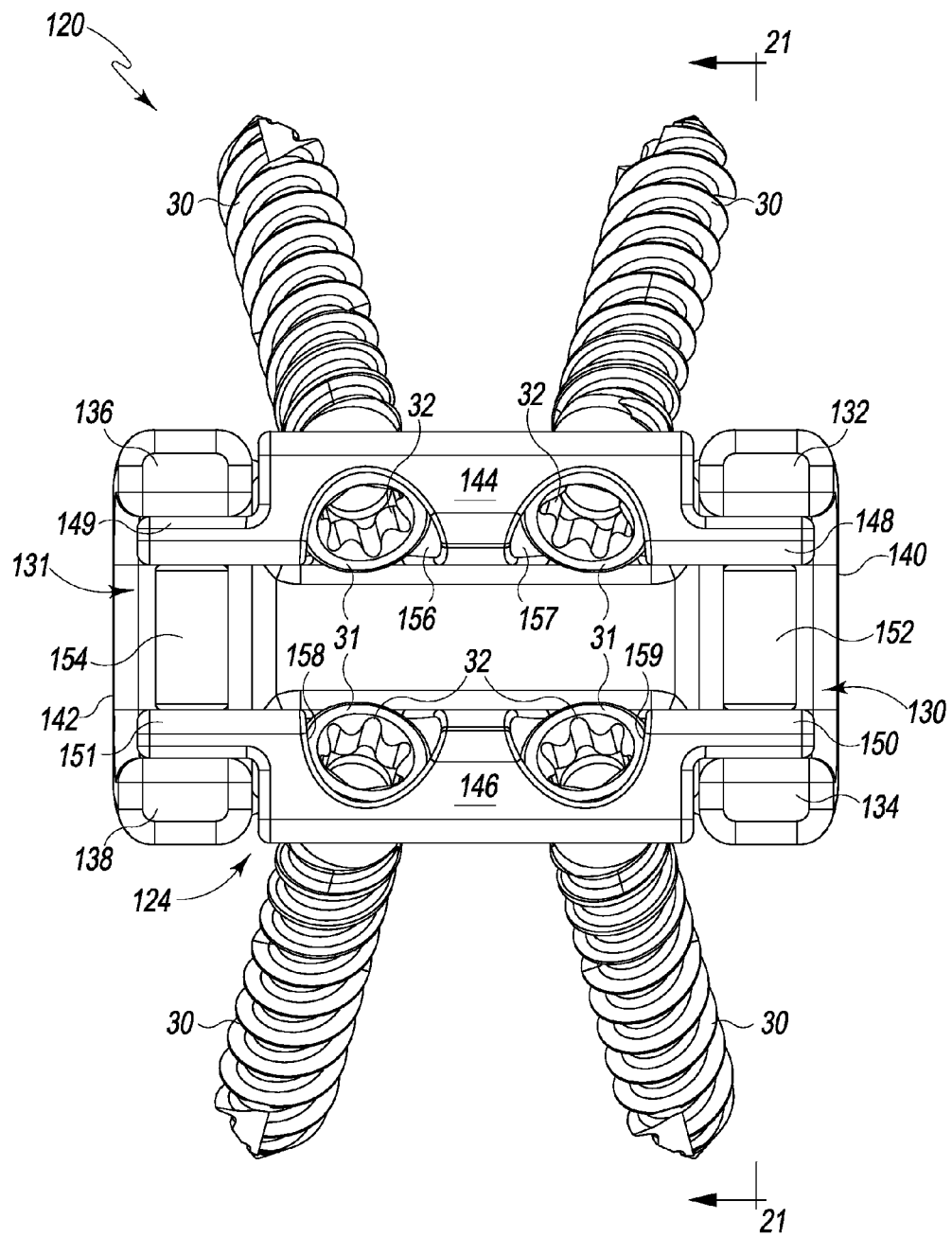
FIG. 20 is a front (anterior) view of an embodiment of a static combined spinal interbody and plate fashioned in accordance with the present principles, the spinal plate formed as a four-screw alignment/tension spine plate.
Figure 21:
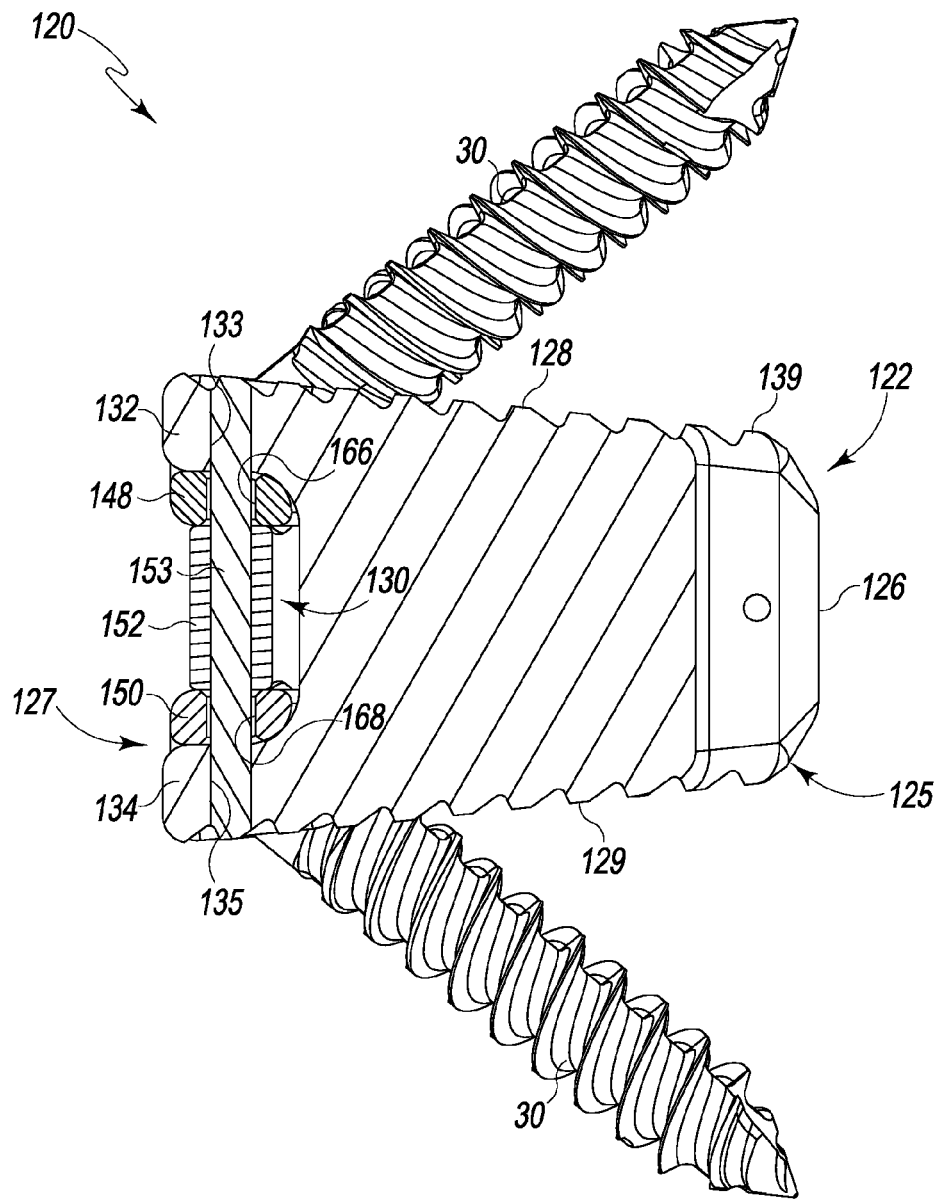
FIG. 21 is a side view of the static combined spinal interbody and four-screw alignment/tension spine plate of FIG. 20 taken along line 21-21 thereof.
Figure 22:
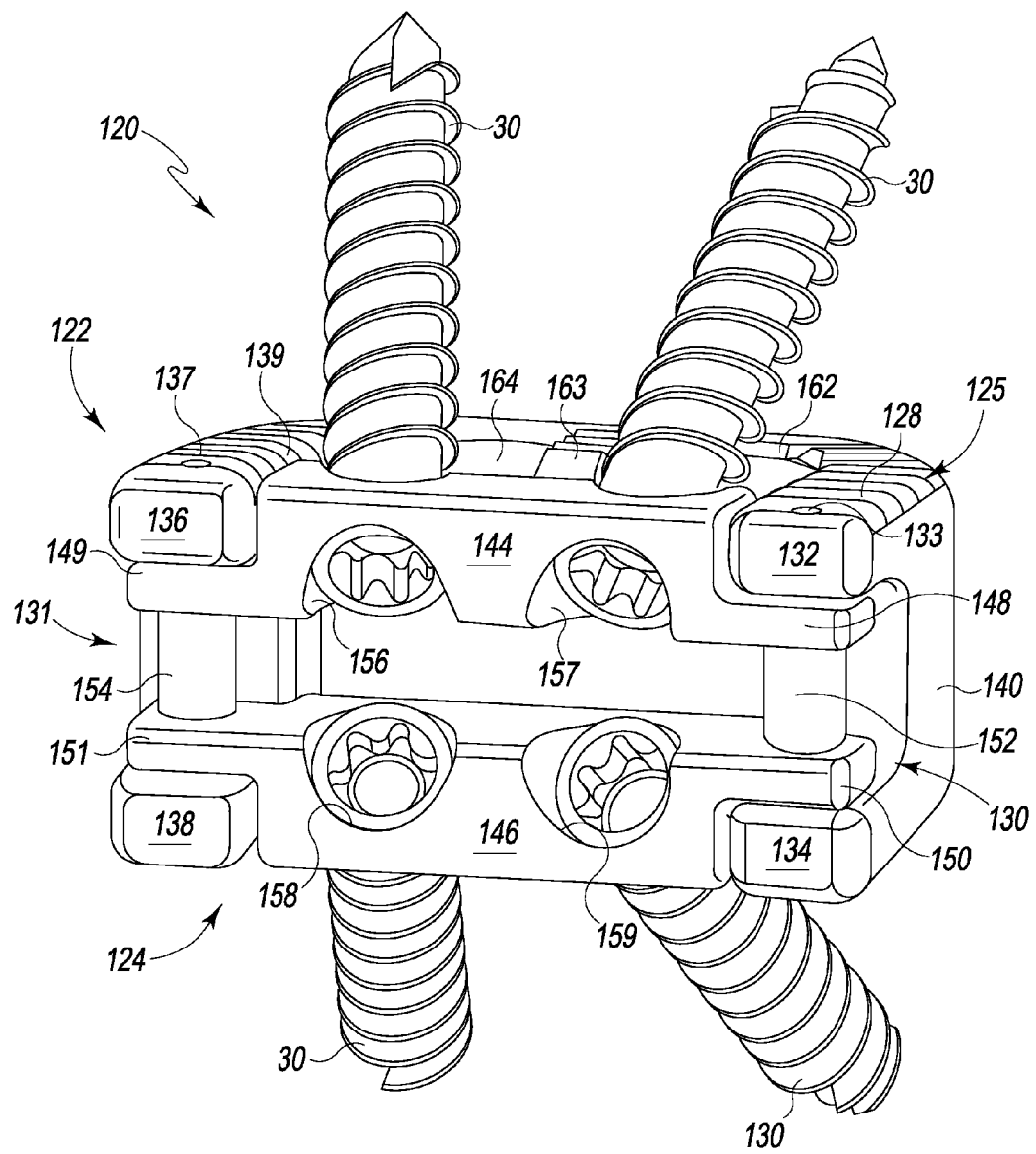
FIG. 22 is a perspective view of the static combined spinal interbody and four-screw alignment/tension spine plate of FIG. 20.

Referring now to FIGS. 20-22, there is depicted various views of another embodiment of a spinal prosthesis comprising a combined, static stand-alone spinal interbody assembly fashioned in accordance with the present principles. The present stand-alone spinal interbody assembly, generally designated 120, provides stabilization and torsional resistance to promote fusion of adjacent vertebrae of the spine. In FIGS. 20-22, the spinal prosthesis 120 is a static stand-alone prosthesis wherein the plates do not translate.

The static, stand-alone interbody assembly 120 is a four-screw spine plate embodiment wherein two screws are used in each adjacent vertebrae for mounting thereof. The assembly 120 is characterized by an interbody 122 and a spine plate 124. The interbody 124 is formed of a body 125 that is sized and configured in larger proportion than the previous interbodies/intervertebral spacers, for reception in an interbody space. The body 125 is thus designed to fit within an interbody space. In the present embodiment, the body 125 is generally D-shaped or semi disc-shaped. It should be appreciated that the body 125 may be configured differently while adhering to the present principles.

The body 125 has a first side 128, a second side 129, a posterior end 126, an anterior end 127, a first lateral side 140 and a second lateral side 142, the nomenclature first and second being arbitrary. The first side 128 may be considered the superior side while the second side 129 may be considered the inferior side. It should be appreciated, however, that the second side may be considered the superior side while the first side may be considered the inferior side. Hereinafter, however, the first side 128 will be considered the superior side while the second side 129 will be considered the inferior side. The body 125 includes first and second cavities 162, 164 that extend from and between the first and second sides 128, 129.

As best seen in FIG. 21, the first side 128 slopes slightly downwardly from the anterior end 127 to the posterior end 126 of the body 125 while the second side 129 slopes slightly upwardly from the anterior end 127 to the posterior end 126 to define a wedge shape. It should be appreciated, however, that the body 125 may not be necessarily wedge-shaped, but instead have a parallel or reversed wedge-shape configuration. Other configurations are contemplated. The first side 128 has a plurality of teeth that are configured so as to slant or angle in the anterior direction. Likewise, the second side 129 has a plurality of teeth that are configured so as to slant or angle in the anterior direction. When installed in the intervertebral space of adjacent vertebrae from the anterior side to the posterior side, the teeth provide an anti back-out mechanism.

The body 125 also includes a first upper flange 132 that extends in the posterior direction from the first lateral side 140 of the body 125 and a first lower flange 134 that extends in the posterior direction from the first lateral side 140 of the body 125. A vertical bore 133 extends through the first upper flange 132 while a vertical bore 135 extends through the first lower flange 134. A pin, dowel, rod or the like 153 extends through the first upper flange bore 133 and the first lower flange bore 135.

The body 125 further includes a second upper flange 136 that extends in the posterior direction from the second lateral side 142 of the body 125 and a second lower flange 138 that extends in the posterior direction from the second lateral side 142 of the body 125. A vertical bore 137 extends through the second upper flange 136 while a vertical bore (not seen) extends through the second lower flange 138. A pin, dowel, rod or the like (not seen) extends through the second upper flange bore 136 and the second lower flange bore (not seen) in like manner to pin 153.

A space 130 is defined between the first upper flange 132 and the first lower flange 134. The space 130 provides an area of translation for one side of each spine plate portion 144, 146. A space 131 is defined between the second upper flange 136 and the second lower flange 138. The space 131 provides an area of translation for another side of the spine plate portions 144, 146. While described below in more detail, the movement of the spine plate portions 144, 146 are rendered immobile or are limited in translation.

The spine plate 124 is characterized by a first spine plate portion 144 and a second spine plate portion 146, with the nomenclature first and second again being arbitrary. The first spine plate portion 144 has a first configured bone screw bore 156 that is sized and configured to receive the head 31 of a bone screw 16 and to allow the axial positioning of the threaded shank 30 of the bone screw 16 to be variable relative to the bone screw bore 156. The first spine plate portion 144 has a second configured bone screw bore 157 that is sized and configured to receive the head 31 of a bone screw 16 and to allow the axial positioning of the threaded shank 30 of the bone screw 16 to be variable relative to the bone screw bore 157. It should be appreciated that the bone screw bores 156, 157 may be configured to provide a fixed angle and/or positioning of the bone screw 16 therein.

The second spine plate portion 146 has a first configured bone screw bore 158 that is sized and configured to receive the head 31 of a bone screw 16 and to allow the axial positioning of the threaded shank 30 of the bone screw 16 to be variable relative to the bone screw bore 158. The second spine plate portion 136 has a second configured bone screw bore 159 that is sized and configured to receive the head 31 of a bone screw 16 and to allow the axial positioning of the threaded shank 30 of the bone screw 16 to be variable relative to the bone screw bore 159. It should be appreciated that the bone screw bores 158, 159 may be configured to provide a fixed angle and/or positioning of the bone screw 16 therein.

The first spine plate portion 144 has a first tang 148 on a first lateral side thereof (proximate the lateral side 140 of the body 125) and a second tang 149 on a second lateral side thereof (proximate the lateral side 142 of the body 125). The first tang 148 includes a bore 166 that is sized to fit about pin 153. The second tang 149 includes a bore therein (not seen) that is sized to fit about a pin (not seen). In this manner, the first plate portion 144 may translate, move or dynamize in the superior/inferior direction if made possible.

The second spine plate portion 146 has a first tang 150 on a first lateral side thereof (proximate the lateral side 140 of the body 125) and a second tang 151 on a second lateral side thereof (proximate the lateral side 142 of the body 125). The first tang 150 includes a bore 168 that is sized to fit about pin 153. The second tang 151 includes a bore therein (not seen) that is sized to fit about the pin (not seen). In this manner, the second plate portion 146 may translate, move or dynamize in the superior/inferior direction in the same manner as first plate portion 144 if made possible.

The spine plate 124 is thus retained by the interbody 122 through capture of the tangs 148, 149, 150, 151 by the respective pins (not shown). The first and second spine plate portions 144, 146 are thus free to move or translate on/along the length of the pins in the superior/inferior direction if permitted. However, a first washer 152 is positioned on the pin 153 between the tang 148 of the first spine plate portion 144 and the tang 150 of the second spine plate portion 146. The first washer 152 is generally cylindrical and is sized to prohibit movement of the tangs 148, 150 and thus the first lateral sides of the first and second spine plate portions 144, 146. Moreover, a second washer 154 is positioned on the pin (not seen) between the tang 149 of the first spine plate portion 144 and the tang 151 of the second spine plate portion 146. The second washer 154 is generally cylindrical and is sized to prohibit movement of the tangs 149, 151 and thus the second lateral sides of the first and second spine plate portions 144, 146. Thus, the spine plate 124 is in a static, fully open, extended, moved, translated or un-dynamized position.

In this position, both of the first and second spine plate portions 144, 146 are translated away from each other the most axial distance that they can. When installed in this position, retention of the spine plate portions 144 and 146 prohibit vertebral compression; therefore, vertebral spacing is retained and/or the spine plate 124 shares the load with the interbody 122. Particularly, there is no further extension movement or dynamization allowed between the spine plate portions and the interbody (i.e. they cannot spread out any more relative to one another). It should be appreciated that the washers 152, 154 may be made axially smaller to permit limited movement of the plates.

Figure 23:
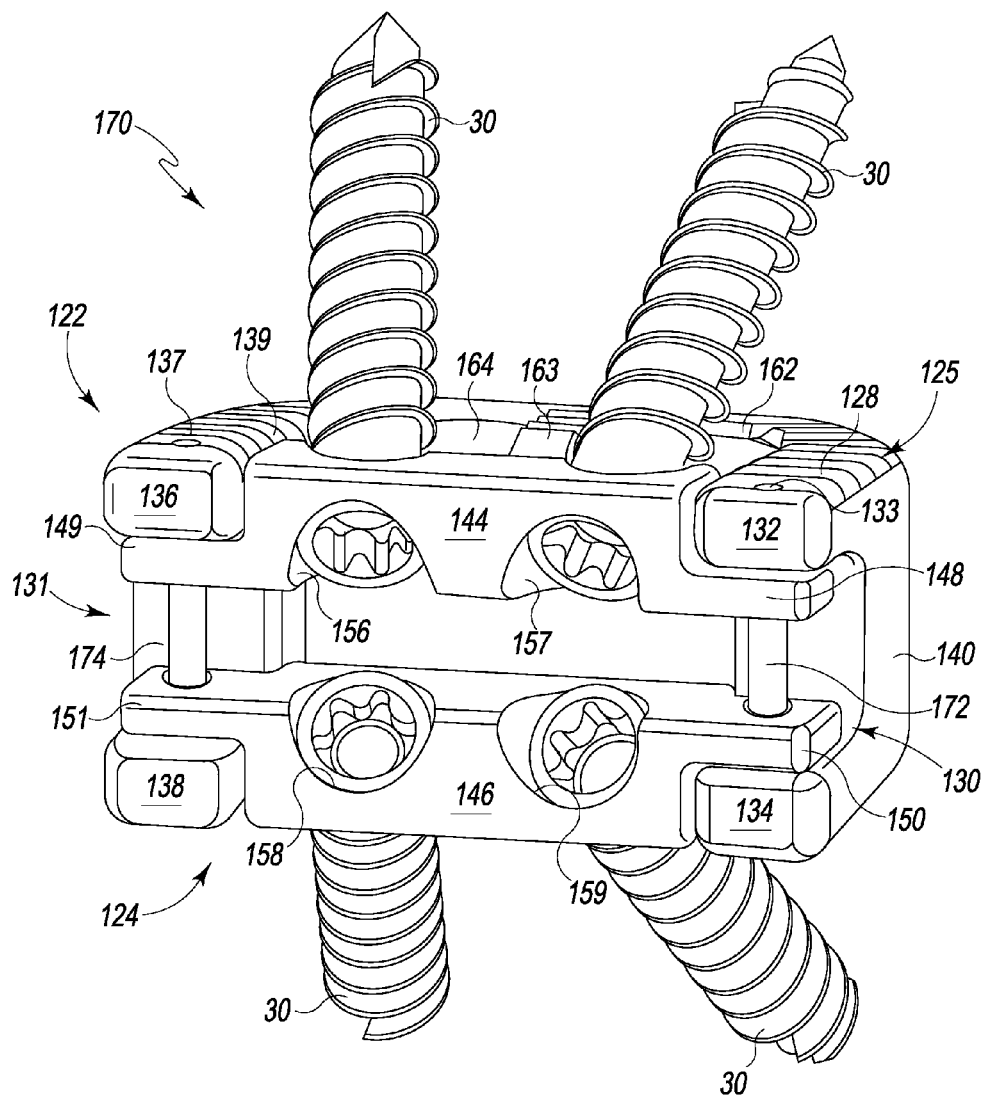
FIG. 23 is a perspective view of another combined spinal interbody and plate fashioned in accordance with the present principles, the spinal plate formed as a four-screw alignment/tension plate and shown in an open or dynamized position.

Referring now to FIG. 23, there is depicted various views of another embodiment of a spinal prosthesis comprising a combined, dynamic stand-alone spinal interbody assembly fashioned in accordance with the present principles. The present stand-alone spinal interbody assembly, generally designated 170, provides stabilization and torsional resistance to promote fusion of adjacent vertebrae of the spine.

The dynamic, stand-alone interbody assembly 170 is a four-screw spine plate embodiment wherein two screws are used in each adjacent vertebrae for mounting thereof. The assembly 170 is characterized by an interbody 122 and a spine plate 124. The interbody 124 is formed of a body 125 that is sized and configured in larger proportion than the previous interbodies/intervertebral spacers, for reception in an interbody space. The body 125 is thus designed to fit within an interbody space. In the present embodiment, the body 125 is generally D-shaped or semi disc-shaped. It should be appreciated that the body 125 may be configured differently while adhering to the present principles.

The body 125 has a first side 128, a second side 129, a posterior end 126, an anterior end 127, a first lateral side 140 and a second lateral side 142, the nomenclature first and second being arbitrary. The first side 128 may be considered the superior side while the second side 129 may be considered the inferior side. It should be appreciated, however, that the second side may be considered the superior side while the first side may be considered the inferior side. Hereinafter, however, the first side 128 will be considered the superior side while the second side 129 will be considered the inferior side. The body 125 includes first and second cavities 162, 164 that extend from and between the first and second sides 128, 129.

While not seen in the figures, the first side 128 slopes slightly downwardly from the anterior end 127 to the posterior end 126 of the body 125 while the second side 129 slopes slightly upwardly from the anterior end 127 to the posterior end 126 to define a wedge shape. It should be appreciated, however, that the body 125 may not be necessarily wedge-shaped, but instead have a parallel or reversed wedge-shape configuration. Other configurations are contemplated. The first side 128 has a plurality of teeth that are configured so as to slant or angle in the anterior direction. Likewise, the second side 129 has a plurality of teeth that are configured so as to slant or angle in the anterior direction. When installed in the intervertebral space of adjacent vertebrae from the anterior side to the posterior side, the teeth provide an anti back-out mechanism.

The body 125 also includes a first upper flange 132 that extends in the posterior direction from the first lateral side 140 of the body 125 and a first lower flange 134 that extends in the posterior direction from the first lateral side 140 of the body 125. A vertical bore 133 extends through the first upper flange 132 while a vertical bore 135 extends through the first lower flange 134. A pin, dowel, rod or the like 172 extends through the first upper flange bore 133 and the first lower flange bore 135.

The body 125 further includes a second upper flange 136 that extends in the posterior direction from the second lateral side 142 of the body 125 and a second lower flange 138 that extends in the posterior direction from the second lateral side 142 of the body 125. A vertical bore 137 extends through the second upper flange 136 while a vertical bore (not seen) extends through the second lower flange 138. A pin, dowel, rod or the like 174 extends through the second upper flange bore 136 and the second lower flange bore (not seen) in like manner to pin 172.

A space 130 is defined between the first upper flange 132 and the first lower flange 134. The space 130 provides an area of translation for one side of each spine plate portion 144, 146. A space 131 is defined between the second upper flange 136 and the second lower flange 138. The space 131 provides an area of translation for another side of the spine plate portions 144, 146.

The spine plate 124 is characterized by a first spine plate portion 144 and a second spine plate portion 146, with the nomenclature first and second again being arbitrary. The first spine plate portion 144 has a first configured bone screw bore 156 that is sized and configured to receive the head 31 of a bone screw 16 and to allow the axial positioning of the threaded shank 30 of the bone screw 16 to be variable relative to the bone screw bore 156. The first spine plate portion 144 has a second configured bone screw bore 157 that is sized and configured to receive the head 31 of a bone screw 16 and to allow the axial positioning of the threaded shank 30 of the bone screw 16 to be variable relative to the bone screw bore 157. It should be appreciated that the bone screw bores 156, 157 may be configured to provide a fixed angle and/or positioning of the bone screw 16 therein.

The second spine plate portion 146 has a first configured bone screw bore 158 that is sized and configured to receive the head 31 of a bone screw 16 and to allow the axial positioning of the threaded shank 30 of the bone screw 16 to be variable relative to the bone screw bore 158. The second spine plate portion 136 has a second configured bone screw bore 159 that is sized and configured to receive the head 31 of a bone screw 16 and to allow the axial positioning of the threaded shank 30 of the bone screw 16 to be variable relative to the bone screw bore 159. It should be appreciated that the bone screw bores 158, 159 may be configured to provide a fixed angle and/or positioning of the bone screw 16 therein.

The first spine plate portion 144 has a first tang 148 on a first lateral side thereof (proximate the lateral side 140 of the body 125) and a second tang 149 on a second lateral side thereof (proximate the lateral side 142 of the body 125). The first tang 148 includes a bore 166 that is sized to fit about pin 172. The second tang 149 includes a bore therein (not seen) that is sized to fit about a pin 174. In this manner, the first plate portion 144 may translate, move or dynamize in the superior/inferior direction along the pins 172, 174.

The second spine plate portion 146 has a first tang 150 on a first lateral side thereof (proximate the lateral side 140 of the body 125) and a second tang 151 on a second lateral side thereof (proximate the lateral side 142 of the body 125). The first tang 150 includes a bore 168 that is sized to fit about pin 172. The second tang 151 includes a bore therein (not seen) that is sized to fit about the pin 174. In this manner, the second plate portion 146 may translate, move or dynamize in the superior/inferior direction in the same manner as first plate portion 144.

The spine plate 124 is thus retained by the interbody 122 through capture of the tangs 148, 149, 150, 151 by the respective pins 172, 174. The first and second spine plate portions 144, 146 are thus free to move or translate on/along the length of the pins 172, 171 in the superior/inferior direction. Both of the first and second spine plate portions 144, 146 can translated away from and towards each other.

While not shown, it should be appreciated that spinal plate portions may optionally include mating ratchet features so that the position of the spinal plate portions is locked between intervals of dynamization and the adjacent vertebrae. The mating ratchet features are positioned on arms of the spinal plate portions.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A spinal implant comprising:
   a spacer formed of a body configured for reception and retention between a first vertebra and second vertebra, the body having a first lateral side, a second lateral side opposite the first lateral side, a first side extending between the first and second lateral sides and configured to engage the first vertebra, a second side extending between the first and second lateral sides opposite the first side and configured to engage the second vertebra, and a cavity defined and substantially enclosed by the first and second sides and the first and second lateral sides, the body defining a first axis;
   a pin extending through the cavity of the spacer between the first and second lateral sides and defining a second axis generally perpendicular to the first axis;
   a spine plate coupled to the spacer, the spine plate comprising:
      a first spine plate portion having a first end and a second end, the first end having a bone screw bore to allow attachment of the first spine plate portion to the first vertebra via a first bone screw, and the second end extending into the cavity between the first and second sides, and coupled to the pin; and
   a second spine plate portion having a first end and a second end, the first end having a second bone screw bore to allow attachment of the second spine plate portion to the second vertebra via a second bone screw, and the second end extending into the cavity between the first and second sides, and coupled to the pin;
   wherein the first spine plate portion and second spine plate portion are configured for translational movement along the first axis and rotational movement about the second axis, wherein at least the translational movement provides adjustable positioning of the first and second spine plate portions relative to the spacer along the first axis to allow the spacer to be affixed to the first and second vertebrae in a plurality of positions, wherein the translational movement and the rotational movement of the second ends of the first and second spine plate portions are contained within the spacer between the first and second sides and the first and second lateral sides.

2. The spinal implant of claim 1, wherein the first spine plate and the second spine plate are connected by the pin for rotational movement relative to each other.

3. The spinal implant of claim 1, wherein:
   the first spine plate portion includes a first angled section between the first end and the second end so that the second end is at a first angle relative to the first end; and the second spine plate portion includes a second angled section between the first end and the second end so that the second end is at a second angle relative to the first end.

4. The spinal implant of claim 3, wherein the first angle is an obtuse angle and the second angle is an obtuse angle.

5. The spinal implant of claim 1, wherein the first bone screw bore is tapered for angled reception of the first bone screw, and the second bone screw bore is tapered for angled reception of the second bone screw.

6. The spinal implant of claim 1, wherein the second end of the first spine plate portion includes a pair of spaced apart arms, and wherein the second end of the second spine plate portion includes an angled arm located between the pair of spaced apart arms of the first spine plate portion.

7. The spinal implant of claim 1, wherein the spacer includes a pair of opposed and aligned bores that are in communication with the cavity and receive ends of the pin.

8. The spinal implant of claim 7, wherein the bores are elongated bores.

9. The spinal implant of claim 8, wherein the elongated bores extend entirely through the first and second lateral sides of the spacer that at least partially define the cavity.

10. A spinal implant comprising:
  a spacer formed of a body configured for reception and retention between a first vertebra and second vertebra, the body having a first lateral side, a second lateral side opposite the first lateral side, a first side extending between the first and second lateral sides and configured to engage the first vertebra, a second side extending between the first and second lateral sides opposite the first side and configured to engage the second vertebra, and a cavity defined and substantially enclosed by the first and second sides and the first and second lateral sides, the body defining a first axis;
  a pin extending through the cavity of the spacer between the first and second lateral sides and defining a second axis generally perpendicular to the first axis;
  a spine plate coupled to the spacer, the spine plate comprising:
    a first spine plate portion having a first end, a second end, and an angled section connecting the first end and the second end so that the first end is at an obtuse angle relative to the second end, the first end having a bone screw bore to allow attachment of the first spine plate portion to the first vertebra via a first bone screw, and the second end located at least partially in the cavity and coupled to the pin; and
    a second spine plate portion having a first end, a second end, and an angled section connecting the first end and the second end so that the first end is at an obtuse angle relative to the second end, the first end having a second bone screw bore to allow attachment of the second spine plate portion to the second vertebra via a second bone screw, and the second end located at least partially in the cavity and coupled to the pin;
  wherein the first spine plate portion and second spine plate portion are configured for translational movement and rotational movement relative to the spacer and to each other, wherein at least the translational movement provides adjustable translating positioning of the first and second spine plate portions relative to the spacer along the first axis to allow the spacer to be affixed to the first and second vertebrae in a plurality of positions and/or allow movement post installation perpendicular to the second axis, and wherein the translational movement and the rotational movement of the second ends of the first and second spine plate portions are contained within the spacer.

11. The spinal implant of claim 10, wherein the second end of the first spine plate portion includes a pair of spaced apart arms, and wherein the second end of the second spine plate portion includes an angled arm located between the pair of spaced apart arms of the first spine plate portion.

12. The spinal implant of claim 10, wherein the spacer includes a pair of opposed and aligned bores that are in communication with the cavity and receive ends of the pin.

13. The spinal implant of claim 12, wherein the bores extend entirely through the first and second lateral sides of the spacer that at least partially define the cavity.

* * * * *